United States Patent [19]
Tang et al.

[11] Patent Number: 6,110,957
[45] Date of Patent: Aug. 29, 2000

[54] SYNTHETIC METHODS FOR THE PREPARATION OF INDOLYLQUINONES AND MONO- AND BIS-INDOLYLQUINONES PREPARED THEREFROM

[75] Inventors: Peng C. Tang, Moraga; G. Davis Harris, Jr., San Francisco, both of Calif.

[73] Assignee: Sugen, Inc., South San Francisco, Calif.

[21] Appl. No.: 09/072,861

[22] Filed: May 5, 1998

Related U.S. Application Data

[62] Division of application No. 08/964,791, Nov. 5, 1997, Pat. No. 5,786,488.
[60] Provisional application No. 60/030,604, Nov. 13, 1996, and provisional application No. 60/042,989, Apr. 14, 1997.
[51] Int. Cl.[7] .................. A61K 31/404; C07D 209/12; C07D 209/42
[52] U.S. Cl. .................. 514/419; 548/469; 548/492; 548/509; 548/510; 548/511; 514/415
[58] Field of Search .................. 548/469, 511, 548/492, 509, 510; 514/415, 419

[56] References Cited

U.S. PATENT DOCUMENTS 3,917,820  11/1975  Brewer et al. .................. 424/122

FOREIGN PATENT DOCUMENTS 63-60966  3/1988  Japan .

OTHER PUBLICATIONS

Yamamoto et al., English translation of Japanese Patent Publication No. 63–60966, Mar. 17, 1988.
Corradini, M.G. et al., *Gazzetta Chimica Italiana* (1989) 119: 153–156.
Young, T.E. and Babbit B. W., *J. Org. Chem.* (1982) 47: 1571–1572.
Colonna, M and Monti, A., *Gazzetta Chimica Italiana* (1982) 92: 1401–1421.
Möhlau, R. and Redlich, A., *Berichte der Deutschen Chemischen Gesellchaft* (1912) 3605–3618.
Colonna et al., CA 59:542c, No. 1, Jul. 8, 1963.
Grazia Corradini et al., CA 111:232499, 1989.
Moehlau et al., Beilstein Reference 1–21–00–00420 of Chem. Ber., 44(1911), p. 3614.
Bu'Lock and Harley–Mason, 1951, "Melanin and Its Precursors. Part II, Model Experiments on the Reactions Between Quinones and Indoles, and Consideration of a Possible Structure for the Melanin Polymer", J. Chem. Soc. London, No. 152, pp. 703–712.

Brewer et al., 1961, "The Production of Cochliodinol and a Related Metabolite by Chaetomium Species", Can. J. Microbiol. 14:861–866.
Jerram et al., 1975, "The Chemistry of Cochliodinol, a Metabolite of Chaetomium Spp.", Can. J. Chem. 53:727–737.
Yamamoto et al., 1976, "Studies on the Metabolic Products of *Aspergillus terreus*. I. Metabolites of the Strain IFO 6123", Chem. Pharm. Bull. 24:1853–1859.
Arai et al., 1981, "Metabolic Products of *Aspergillus terreus* IV. Metabolites of the Strain IFO 8835. (2) The Isolation and Chemical Structure of Indolyl Benzoquinone Pigments", Chem. Pharm. Bull. 29:961–969.
Arai et al., 1981, "Metabolic Products of *Aspergillus terreus* V. Demethylation of Asterriquinones", Chem. Pharm. Bull. 29:991–999.
Arai et al., 1981, "Metabolic Products of *Aspergillus terreus* VI. Metabolites of the Strain IFO 8835. (3) The Isolation and Chemical Structures of Colorless Metabolites", Chem. Pharm. Bull. 29:1005–1012.
Shimizu et al., 1982, "Antitumor Effect and Structure–Activity Relationship of Asterriquinone Analogs", Gann 73:642–648 (Chem. Abstr. 97:174470w).
Shimizu et al., 1982, "Antitumor Activity of Asterriquinones from Aspergillus Fungi", Chem. Pharm. Bull. 30:1896–1899 (Chem. Abstr. 97:103877y).
Young and Babbitt, 1982, "2–(2–Methyl–3–Indolyl)–1, 4–Benzoquinone, a Reversible Redox Substrate at the Carbon–Paste Electrode in Acidic Aquenous–Ethanolic Medic", J. Org. Chem.47:1571–1572 (Chem. Abstr. 96:151191w).
Sekita, 1983, "Isocochliodinol and Neocochliodinol, Bis(3–Indolyl)–Benzoquinones from Chaetomium Spp.", Chem. Pharm. Bull. 31:2998–3001.
Horcher et al., 1986, "Biologically Active Products from Mold Fungi. 35. Total Synthesis of Cochliodinol", Liebigs Ann. Chem. 10:1765–1771 (in German with translation).
Arai et al., 1990, "Metabolic Products of *Aspergillus terreus*. X. Biosynthesis of Asterriquinones", Chem. Pharm. Bull. 38:2929–2932.
Kaji et al., 1995, "Partial Deacetylation of Asterriquinone Diacetate by Aqueous Sodium Bicarbonate in Pyridine", Chem. Pharm. Bull. 43:1818–1820.

*Primary Examiner*—Laura L. Stockton
*Attorney, Agent, or Firm*—Pennie & Edmonds LLP

[57] ABSTRACT

The present invention relates to novel synthetic methods for the preparation of indolylquinones. The methods of the present invention are directed to synthetic reactions involving indoles and halo-quinones in solvent and in the presence of a metal carbonate. The invention also relates to bis- and mono-indolylquinones of high purity and pharmaceutical compositions containing the same.

6 Claims, No Drawings

SYNTHETIC METHODS FOR THE PREPARATION OF INDOLYLQUINONES AND MONO- AND BIS-INDOLYLQUINONES PREPARED THEREFROM

This is a division, of application Ser. No. 08/964,791, filed Nov. 5, 1997 now U.S. Pat. No. 5,786,488 which claims the benefit of U.S. Provisional Application No. 60/030,604 filed Nov. 13, 1996 and U.S Provisional Application No. 60/042,989 filed Apr. 14, 1997.

1. INTRODUCTION

The present invention relates to novel synthetic methods for the preparation of both known and novel indolylquinones. Many indolylquinones, in particular the class of indolylquinones known as the asterriquinones, have utility in the treatment of cell proliferative disorders such as cancer. In addition, many indolylquinones are known to be useful as dyes. Finally, indolylquinones are also known to exhibit antifungal and antibacterial properties. However, in general, indolylquinones are isolated from natural sources and are not prepared synthetically. The present invention is directed to a synthetic method for the preparation of indolylquinones, and to novel compounds prepared using said method. In particular, the methods of the present invention are directed to synthetic reactions involving indoles and halo-quinones in solvent and in the presence of a metal carbonate. These methods provide a direct and simple means of preparing the compounds of interest, indolylquinones.

2. BACKGROUND OP THE INVENTION 2.1 Isolation From Natural Sources and Therapeutic Utility of Indolylquinones Research interest concerning indolylquinones grew out of early observations that extracts of Chaetomium exhibited antibiotic properties. These observations led researchers to attempt the isolation of active species from cultures of these microorganisms. For example, Brewer et al. disclose the isolation of a purple pigment, which was termed cochliodinol, from isolates of *Chaetomium cochliodes* and *Chaetomium globosum* (1968, "The Production of Cochliodinol and a Related Metabolite by Chaetomium Species," *Can. J. Microbiol.* 14:861–866). Brewer et al. also disclose the synthetic conversion of cochliodinol to a diacetate compound. Id. Further, the antifungal properties of cochliodinol have also been documented (Meiler et al., 1971, "The Effect of Cochliodinol, a Metabolite of *Chaetomium cochliodes* on the Respiration of Microspores of *Fusarium oxysporum*," *Can. J. Microbiol.* 17: 83–86).

The structure of cochliodinol was elucidated by Jerram et al. in 1975. (1975, "The Chemistry of Cochliodinol, a Metabolite of Chaetomium spp.," *Can. J. Chem.* 53:727–737). Jerram et al. reported the structure of cochliodinol as: 2,5-dihydroxy-3,6-di(5'-(2"-methylbut-$\Delta^{2"}$-ene)-indolyl-3')-cyclohexadiene-1,4-dione. The conversion of cochliodinol to various other derivatives, including its dimethyl and diacetyl analogues, was also disclosed. Id. Some of these derivatives were highly colored and suitable for use as dyes, while others were colorless. Id. Sekita discloses the isolation of other bis(3-indolyl)-dihydroxybenzoquinones, including isocochliodinol and neocochliodinol from *Chaetomium muroum* and *C. amygdalisporum* (1983, "Isocochliodinol and Neocochliodinol, Bis(indolyl)-benzoquinones from Chaetomium spp.," *Chem. Pharm. Bull.* 31(9): 2998–3001).

Despite the therapeutic potential of cochliodinol and its derivatives, efficient methods suitable for large scale production of these compounds have remained elusive. U.S. Pat. No. 3,917,820 to Brewer et al. discloses the purple pigment cochliodinol and a process for its production by culturing various types of Chaetomium under aerobic conditions. However, the methods of Brewer require long incubation periods for cochliodinol production (2–8 days), the use of benzene, a known carcinogen, to effect chromatographic separation of cochliodinol from the culture and are limited to the few naturally occurring compounds. Moreover, Brewer discloses the isolation of only small quantities (0.75 grams) of cochliodinol from Chaetomium.

Another class of indolylquinones known as the asterriquinones in which the nitrogen of the indole ring is substituted, has been shown to exhibit antitumor activity. Arai et al. proposed the general name "asterriquinones" for the class of indolylquinones based upon asterriquinone (1981, "Metabolic Products of *Aspergillus terreus* IV. Metabolites of the Strain IFO 8835. (2) The Isolation and Chemical Structure of Indolyl Benzoquinone Pigments," *Chem. Pharm. Bull.* 29(4): 961–969). It should be noted that as used herein, the term "asterriquinone" has a more general meaning, and is used interchangeably with the term "indolylquinone." Yamamoto et.al. disclose the antitumor activity of asterriquinone, i.e., 2,5-bis[N-(1",1"-dimethyl-2"-propenyl)indol-3'-yl]-3,6-dihydroxy-1,4-benzoquinone, and its isolation from the fungus *Aspergillus terreus* (1976, "Antitumor Activity of Asterriquinone, a Metabolic Product from *Aspergillus terreus*," *Gann* 67:623–624).

Arai et al. disclose the isolation and characterization of 11 different kinds of bisindolyl-dimethoxyl-p-benzoquinones from *Aspergillus terreus*. Id. The isolation and structural determination of a number of other asterriquinones have also been reported. (Arai et al. 1981, "Metabolic Products of *Aspergillus terreus* VI. Metabolites of the Strain IFO 8835. (3) the Isolation and Chemical Structures of Colorless Metabolites," *Chem. Pharm. Bull.* 29(4): 1005–1012; Kaji et al., 1994, "Four New Metabolites of Aspergillus Terreus", *Chem. Pharm. Bull.* 42(8): 1682–1684). However, the separation of asterriquinones is troublesome because there are so many kinds of homologous pigments in the Aspergillus extracts. Moreover, the chromatographic purification of asterriquinones is typically carried out using benzene, a known carcinogen, as a solvent. Finally, only milligram quantities of asterriquinones have actually been isolated from these natural sources.

In view of their potential as anticancer agents, research has been directed to determination of the relationship between structure and antitumor activity of asterriquinones. For example, Arai et al. reported a study in which hydroxyl benzoquinone derivatives obtained by demethylation of bisindolyl-dimethoxyl-p-benzoquinones were found to have greater antitumor activity than the methoxyl derivatives (1981, "Metabolic Products of *Aspergillus terreus* V. Demethylation of Asterriquinones," *Chem. Pharm. Bull.* 29(4): 991–999). Shimizu et al. noted that the presence of free hydroxyl groups in the benzoquinone moiety, as well the number and position of tert-, isopentenyl, or both pentyl groups, seems to have an effect on the antitumor activity of the compound (1982, "Antitumor Effect and Structure-Activity Relationship of Asterriquinone Analogs," *Gann* 73: 642–648). In an attempt to obtain information towards the development of more potent asterriquinone derivatives, Shimizu et al. conducted an investigation into the structure-activity relationship of asterriquinones in which the action mechanism of asterriquinone in its antitumor activity with reference to its interaction with DNA molecules and the plasma membrane of tumor cells was studied (1990, "Interaction of Asterriquinone with Deoxyribonucleic Acid in Vitro," *Chem. Pharm. Bull.* 38(9): 2617–2619). It was reported that a correlation exists between the pKa value of the asterriquinone derivative and its antitumor activity. Id. Maximum antitumor activity was observed for compounds with pKa's in the range of 6–7. Id.

Analysis of structure-activity relationships has led to attempts to obtain compounds with more potent antitumor activity by chemical modification of asterriquinone and related compounds isolated from natural sources (Shimizu et al., 1982, "Antitumor Activity of Asterriquinones from Aspergillus Fungil IV. An Attempt to Modify the Structure of Asterriquinones to Increase the Activity," *Chem. Pharm. Bull.* 30(5): 1896–1899). Although benzoquinone derivatives having aziridinyl groups in the molecule such as mitomycin C, carbazilquinone or "E 39" are well known potent anticancer agents, replacement of the functional groups at the 3 and 6 positions in the benzoquinone moiety of asterriquinone failed to enhance its antitumor potency. Id. Similarly, the introduction of an ethyleneimino group into the molecule did not increase antitumor activity. A dimethylallyl derivative of asterriquinone showed moderate activity against the ascites and solid tumors of Ehrlich carcinoma, while an allyl derivative did not. It was suggested that in order to enhance the antitumor activity, it may be necessary not only to alter the pKa value by alkylation, but also to introduce hydrophilic groups into the molecule.

Most recently, in addition to their demonstrated antitumor activity, asterriquinone and some of its analogues have also been shown to be strong inhibitors of HIV-reverse transcriptase (Ono et al., 1991, "Inhibition of HIV-Reverse Transcriptase Activity by Asterriquinone and its Analogues," *Biochem. Biophys. Res. Commun.* 174(1): 56–62).

2.2 Cancer and Signal Transduction

As mentioned above, indolylquinones have utility as antitumor agents for the treatment of cancer and other cell proliferative disorders. These compounds are believed to arrest the growth of tumors by interfering with the signal transduction pathways that regulate cell proliferation and differentiation.

Protein phosphorylation is a common regulatory mechanism used by cells to selectively modify proteins carrying signals that regulate cell proliferation and differentiation. The proteins that execute these biochemical modifications are a group of enzymes known as protein kinases. They may further be defined by the amino acid that they target for phosphorylation. One group of protein kinases are the tyrosine kinases (PTKs) which selectively phosphorylate a target protein on its tyrosine residues.

Protein tyrosine kinases comprise a large family of proteins, including many growth factor receptors and potential oncogenes. Tyrosine kinases can be cytoplasmic, non-receptor-type enzymes and act as a key component of a signal transduction pathway which regulates cell functions such as cell division, differentiation and survival.

Adaptor proteins are intracellular proteins having characteristic conserved peptide domains (SH2 and/or SH3 domains, as described below) which are critical to the signal transduction pathway. Such adaptor proteins serve to link protein tyrosine kinases, especially receptor-type protein tyrosine kinases to downstream intracellular signalling pathways such as the RAS signalling pathway. It is thought that such adaptor proteins may be involved in targeting signal transduction proteins to the correct site in the plasma membrane or subcellular compartments, and may also be involved in the regulation of protein movement within the cell.

The profound cellular effects mediated by tyrosine kinases and adaptor molecules have made them attractive targets for the development of new therapeutic molecules. It is known, for example, that the overexpression of tyrosine kinases, such as HER2, can play a decisive role in the development of cancer (Slamon, D. J., et al. , 1987, *Science*, 235:177–182) and that antibodies capable of blocking the activity of this enzyme can abrogate tumor growth. (Drebin, et al. 1988, *Oncogene* 2:387–394). Blocking the signal transduction capability of tyrosine kinases such as Flk-1 and the PDGF receptor have been shown to block tumor growth in animal models (Millauer, B., et al. 1994, *Nature* 367:577; Ueno, H., et al. 1991, *Science* 252:844–848).

Despite great interest in the various therapeutic and other utilities of indolylquinones such as asterriquinones, research into the therapeutic activities of indolylquinones and efforts to obtain indolylquinones with enhanced therapeutic activity have both been limited by the lack of reliable sources for these compounds. Indeed, isolation of indolylquinones from natural sources requires multiple steps and produces only milligram quantities of the target molecules. Further, evaluation of the activities of novel indolylquinones has necessarily been confined to those compounds which can be obtained by chemical modification of known compounds that can be isolated from natural sources. Clearly, a synthetic routine to these compounds would be invaluable to the art.

2.3 Synthesis of Cochliodinol

A synthetic route to an indolylquinone, cochliodinol, has been reported by Hörcher et al. This route is a complex, multi-step, low-yield process for the total synthesis of cochliodinol (1986, "Totalsynthese des Cochliodinols", *Liebigs. Ann. Chem.* 1765–1771). The Hörcher method involves an unusual solid state reaction of bromanil (2,3,5, 6-tetrabromo-1,4-quinone) with 5-bromoindole in the presence of aluminum oxide and potassium carbonate in a dry box at 105° C. This solid state reaction yields about 11% of 2,5-dibromo-5,6-bis(5-bromo-3-indolyl)-1,4-quinone. The 2,5-dibromo-5,6-bis(5-bromo-3-indolyl)-1,4-quinone is then treated with benzalcohol and sodium hydroxide to give 2,5-bis(benzyloxy)-3,6-bis(5-bromo-3-indolyl)-1,4-quinone in 45% yield. This product is then reacted with hydrogen gas in the presence of a 10% Pd on activated charcoal catalyst, followed by treatment with acetic anhydride in pyridine to give 1,2,4,5-tetracetoxy-3,6-bis(5-bromo-3-indolyl) benzene. Reaction of this compound with a complex of isopentenyl bromide and tetracarbonyl nickel gives 1,2,4,5-tetracetoxy-3,6-bis[5-(3-methyl-2-butenyl)3-indolyl] benzene. This compound is then reacted with sodium hydroxide and oxygen to give cochliodinol.

According to Hörcher et al., the reaction of bromanil with certain substituted indoles is problematic. Hörcher et al. report that earlier attempts to react a p-benzoquinone with 2-methylindole resulted in only monoindolequinones in very low yields. Attempts to react bromanil with 5-(2-methylbut-2-en-4-yl)-indole were also reported by Hörcher to be unsuccessful due to the instability of the unsaturated side chain vis-a-vis the dehydrogenating bromanil. To overcome this difficulty, Hörcher reacted bromanil with 5-bromoindole instead of 5-(2-methylbut-2-en-4-yl), followed by introduction of the 2-methylbut-2-en-4-yl group at the end of the synthesis, requiring the additional step of reacting the 5,5'-dibromo-bis-indolylquinone with the complex of isopentenyl bromide and tetracarbonyl nickel, which substitutes the bromine atoms with 2-methylbut-2-en-4-yl groups.

Hörcher et al. report that this method resulted in isolation of only milligram quantities of cochliodinol in a very low overall yield. However, Hörcher et al. indicate that conducting the initial reaction of bromanil with 5-bromoindole in smaller batches results in better yields. This suggests that the methods of Hörcher et al. are unsuited for production of bis-indolylquinones on a large scale. In addition, as applied to the production of bis-indolylquinones in general, the methods of Hörcher et al. would be prohibitively multistep, and would likely result in isolation of only milligram quantities of the target indolylquinones. Moreover, these methods require high temperature and manipulation in dry box.

Accordingly, despite the great interest in indolylquinones, there is a lack of feasible large scale synthetic routes for obtaining these compounds. Thus, there is a need in the art for a fast, efficient synthetic method for making indolylquinones in preparative quantities. Further, there is a need for synthetic means of producing known indolylquinones previously available only in milligram quantities from natural sources. Moreover, there is a need in the art for a synthetic method that may be manipulated easily to produce a wide variety of structurally diverse novel indolylquinones, so that structure-activity relationships may be further elucidated, and new, perhaps more therapeutically useful indolylquinones may be developed.

3. SUMMARY OF THE INVENTION

The present invention provides a method for the synthesis of indolylquinones which comprise reacting a substituted or unsubstituted 2,5-dihalo-1,4-benzoquinone with one or more substituted or unsubstituted indoles in a polar organic solvent and in the presence of metal carbonate.

In one embodiment, the present invention provides a method for preparing a symmetrical indolylquinone compound of the formula I:

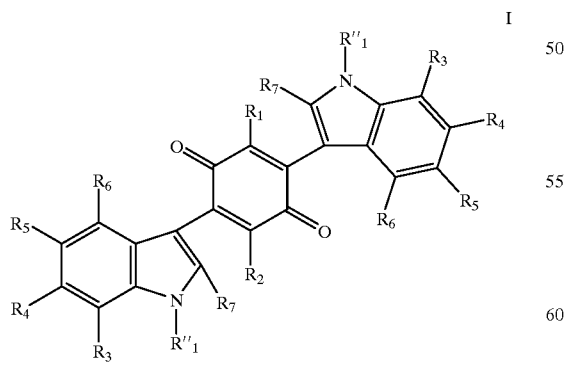

wherein: R1 and R2 are each independently Br, Cl, F, I, H, OH or —OCOR, wherein R is, lower alkyl, aryl or alkylaryl; R"1 is H, $C_1$–$C_7$ alkyl, $C_2$–$C_7$ alkenyl, $C_2$–$C_7$ alkynyl, arylalkyl or aryl; and R3 to R7 are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7. R1 and R2 are preferably Br, Cl, F or H; and least preferably OH. The method comprises reacting a substituted or unsubstituted 2,5-dihalo-1,4-benzoquinone, preferably a 2,5-dibromo-1,4-benzoquinone compound of the formula II:

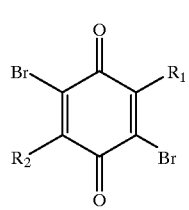

wherein R1 and R2 are as defined above; with at least one indole of the formula III:

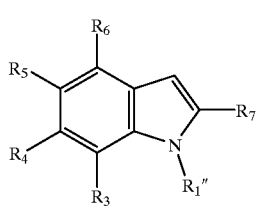

wherein R"1 and R3–R7 are as defined above. The reaction is carried out in a polar organic solvent and in the presence of metal carbonate under mild conditions which are further discussed below.

The method may further comprise reacting the indolylquinone compound of formula I with an alkali metal hydroxide to produce a compound of the formula IV:

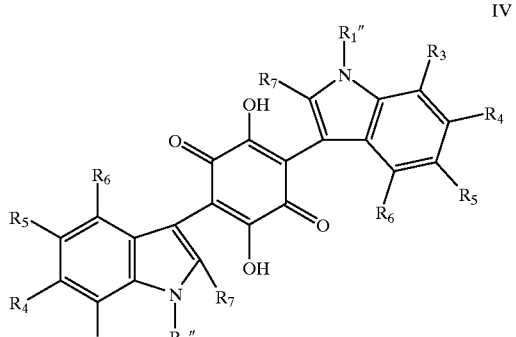

Further, the invention encompasses reacting the indolylquinone compound of formula I wherein R1 and R2 are Br with an alkali metal hydroxide and an alcohol of the formula R'OH, wherein R' is lower alkyl or alkylaryl, to produce an indolylquinone compound of the formula:

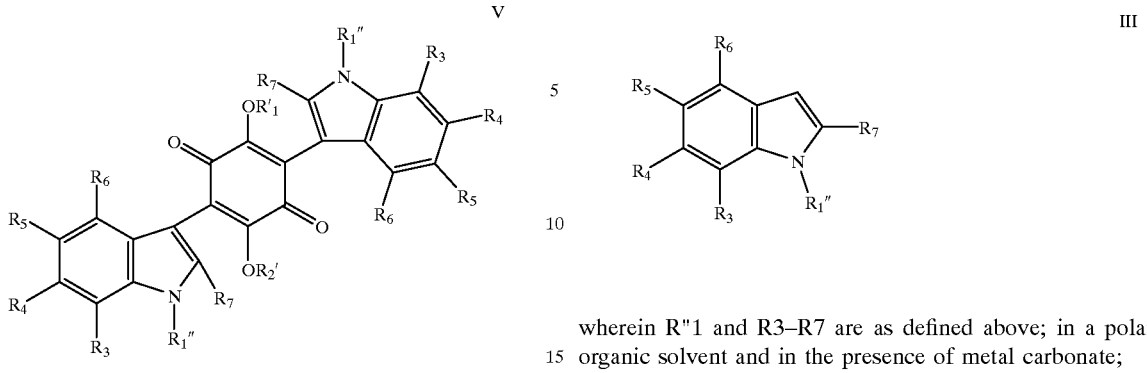

wherein R'1 and R'2 are each independently lower alkyl, aryl or alkylaryl.

In another embodiment, the present invention provides a method for preparing an asymmetrical indolylquinone compound of the formula VI:

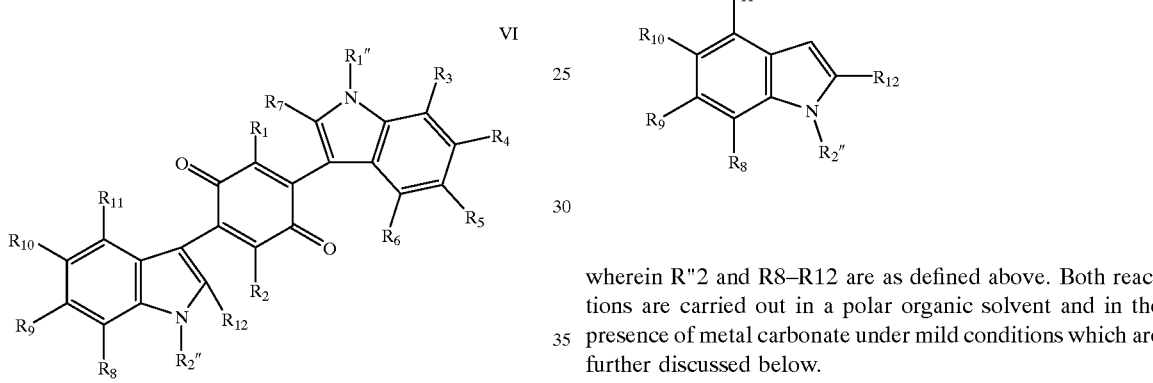

wherein: R1 and R2 are each independently Br, Cl, F, I, H, OH, or —OCOR, wherein R is lower alkyl, aryl or alkylaryl; R"1 and R"2 are each independently H, $C_1$–$C_7$ alkyl, $C_2$–$C_7$ alkenyl, $C_2$–$C_7$ alkynyl, arylalkyl or aryl; and R3 to R12 are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7. R1 and R2 are preferably Br, Cl, F or H; and least referably OH. The principal steps of the method comprise:

(a) reacting a substituted or unsubstituted 2,5-dibromo-1,4-benzoquinone compound of the formula II:

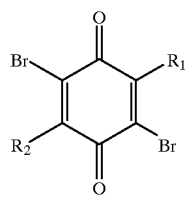

wherein R1 and R2 are as defined above; with one equivalent of a first indole of the formula III:

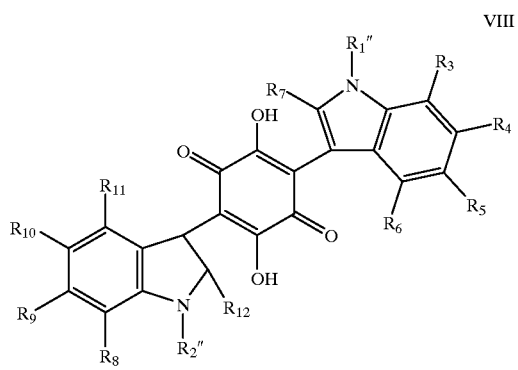

wherein R"1 and R3–R7 are as defined above; in a polar organic solvent and in the presence of metal carbonate;

(b) reacting the intermediate product of step (a) with one equivalent of a second indole of the formula IV:

wherein R"2 and R8–R12 are as defined above. Both reactions are carried out in a polar organic solvent and in the presence of metal carbonate under mild conditions which are further discussed below.

The invention also encompasses further reacting the indolylquinone compound of formula VI with an alkali metal hydroxide to produce a compound of the formula VIII:

wherein R"1, R"2 and R3–R12 are as defined above.

Further, the invention encompasses reacting the indolylquinone of formula VI wherein R1 and R2 are Br, F, Cl or I with an alkali metal hydroxide and an alcohol of the formula R'OH, wherein R' is lower alkyl or alkylaryl, to produce an indolylquinone compound of the formula IX:

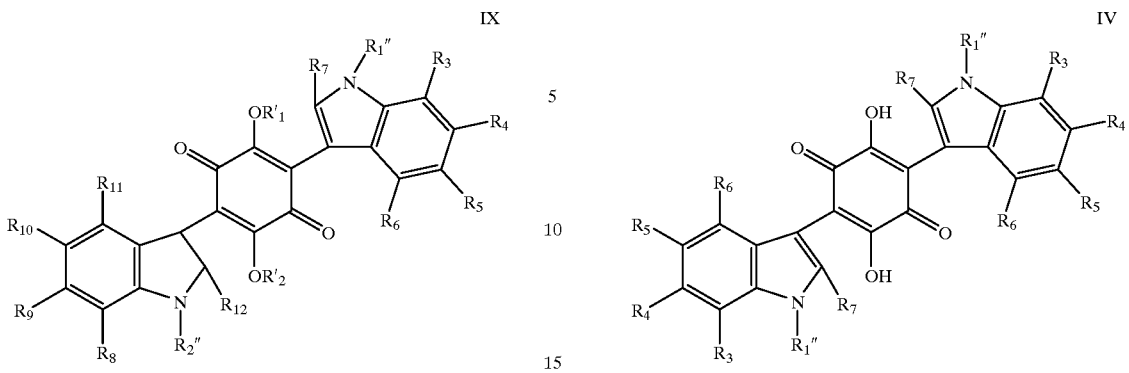

wherein R'1 and R'2 are each independently lower alkyl, aryl or alkylaryl.

In yet another embodiment, the present invention provides a method for preparing an indolylquinone compound of the formula X:

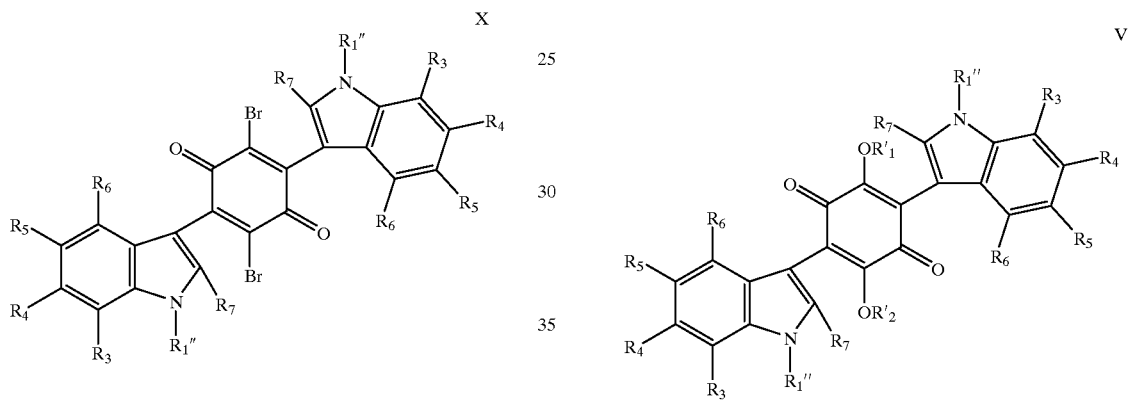

wherein: R"1 is H, $C_1$–$C_7$ alkyl, $C_2$–$C_7$ alkenyl, $C_2$–$C_7$ alkynyl, arylalkyl or aryl4 and R3 to R7 are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl,
wherein n is an integer of 0 to 12, preferably 1–7, and m is an integer of 0 to 12, preferably 1–7. This embodiment of the inventive method involves reacting 2,3,5,6-tetrabromo-1,4-benzoquinone with at least one indole of the formula:

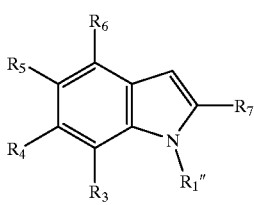

wherein R"1 and R3–R7 are as defined above. The reaction is carried out in a polar organic solvent in the presence of metal carbonate.

The method also encompasses further reacting the indolylquinone compound of formula X with an alkali metal hydroxide to produce a compound of the formula:

wherein R3–R7 are as defined above. Further, the invention also encompasses a method which further comprises reacting the indolylquinone compound of formula X with an alkali metal hydroxide and an alcohol of the formula R'OH, wherein R' is lower alkyl or alkylaryl, to produce an indolylquinone compound of the formula:

wherein R'1 and R'2 are each independently lower alkyl, aryl or alkylaryl.

In yet another embodiment, the present invention provides a method for preparing an indolylquinone compound of the formula XIV:

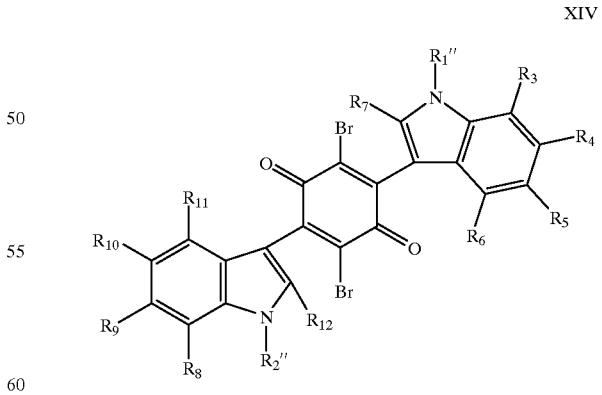

wherein: R"1 and R"2 are each independently H, $C_1$–$C_7$ alkyl, $C_2$–$C_7$ alkenyl, $C_2$–$C_7$ alkynyl, arylalkyl or aryl; and R3 to R12 are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer of 0 to 12, preferably 1–7, and m is an integer of 0 to 12, preferably 1–7. This embodiment of the inventive method involves reacting 2,3,5,6-tetrabromo-1,4-benzoquinone with one equivalent of a first indole of the formula III:

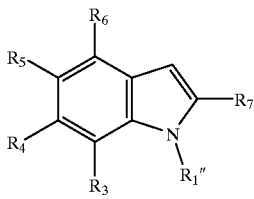

III wherein R"1 and R3–R7 are as defined above; in a polar organic solvent and in the presence of metal carbonate;

reacting the intermediate product of step (a) with one equivalent of a second indole of the formula VII:

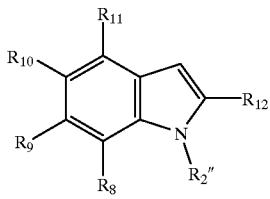

VII wherein R"2 and R8–R12 are as defined above. Both reactions are carried out in a polar organic solvent and in the presence of metal carbonate under mild conditions which are further discussed below.

The invention also encompasses further reacting the indolylquinone compound of formula XIV with an alkali metal hydroxide to produce a compound of the formula VIII:

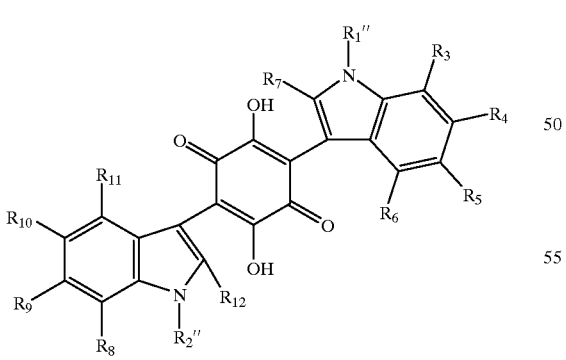

VIII wherein R"1, R"2 and R3–R12 are as defined above.

Further, the invention encompasses reacting the indolylquinone of formula VI wherein R1 and R2 are Br, F, Cl or I with an alkali metal hydroxide and an alcohol of the formula R'OH, wherein R' is lower alkyl or alkylaryl, to produce an indolylquinone compound of the formula IX:

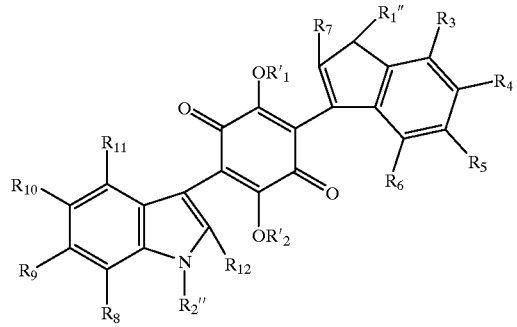

IX wherein R'1 and R'2 are each independently lower alkyl, aryl or alkylaryl.

In still another embodiment, the present invention provides a method for preparing a mono-indolylquinone compound of the formula XI:

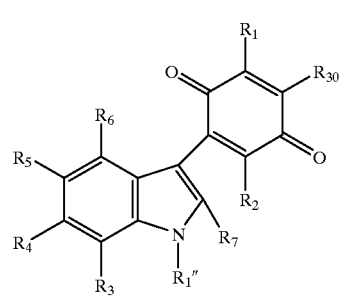

XI wherein R1, R2 and R30 are each independently Br, Cl, F, I, HI OH or —OCOR, wherein R is lower alkyl, aryl or alkylaryl;

R"1 is H, $C_1$–$C_7$ alkyl, $C_2$–$C_7$ alkenyl, $C_2$–$C_7$ alkynyl, arylalkyl or aryl; and R3 to R7 are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12 and m is an integer from 0 to 12. This method comprises reacting a substituted or unsubstituted 2,5-dibromo-1,4-benzoquinone compound of the formula:

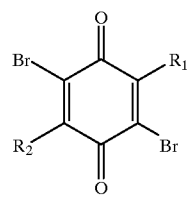

II wherein R1 and R2 are as defined above, with one indole of the formula

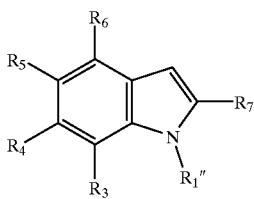

III wherein R"1 and R3–R7 are as defined above. The reaction is carried out in a polar organic solvent and in the presence of metal carbonate.

The method of the present invention may further comprise reacting the indolylquinone compound of formula XI with an alkali metal hydroxide to produce a compound of the formula:

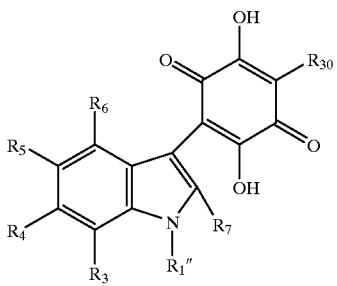

XII wherein R30 and R3–R7 are as defined above.

The method may further comprise reacting the indolylquinone compound of formula XI wherein R1, R2 and R30 are Br, F, Cl or I with a mixture of an alkali metal hydroxide and an alcohol of the formula R'OH, wherein R' is lower alkyl or alkylaryl, to produce an indolylquinone compound of the formula:

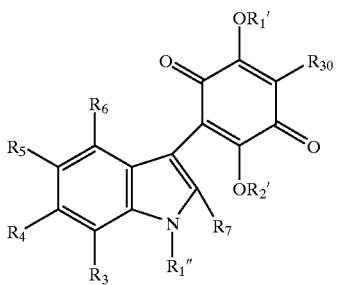

XIII wherein R'1 and R'2 are each independently lower alkyl, aryl or alkylaryl.

In another embodiment, the present invention further encompasses methods for producing large quantities of known, naturally occurring asterriquinones in high purity and in high yield. In yet another embodiment, the present invention is directed to known, synthetically prepared naturally occurring asterriquinones of high purity which are obtainable in large quantities and in high yield. The invention also encompasses the preparation of novel monoindolylquinones, i.e., compounds substituted with only one indole, and the imonoindolylquinone compounds, as described below.

Other features and advantages of the invention will be apparent from the following description of the preferred embodiments thereof, and from the claims.

4. DETAILED DESCRIPTION OF THE INVENTION

As mentioned above, the present invention relates to a synthetic route for the preparation of a wide variety of indolylquinones including asterriquinone compounds having interesting antitumor activity. As a result, the invention provides a major contribution to the art in that naturally occurring compounds with important therapeutic properties can be prepared in large quantities, e.g., quantities of about 1 gram or more, with purity in excess of about 95% and in high yield. The availability of large quantities allows the skilled artisan to more quickly and easily test these naturally occurring compounds. Prior to the present invention, such compounds were isolated from natural sources in limited quantities (e.g., about 750 mg or less) and low purity (e.g., less than about 95%). With the present invention, large quantities can more easily be obtained and the purification of complex natural product mixtures is avoided. Finally, the present invention provides a means for preparing novel analogues of the naturally occurring indolylquinones, which analogues may prove to be of greater interest than the naturally occurring compounds for their therapeutic activity or other properties.

More specifically, the present invention provides a solvent based reaction of indoles and haloquinones in the presence of metal carbonate. It has been discovered that the reaction of indoles and halo-quinones using a polar organic solvent and metal carbonate provides a rapid and efficient reaction under mild conditions, which include but are not limited to mild temperatures, short reaction times and standard/ambient pressures. Thus, the present method is well suited for large scale and commercial production of indolylquinones.

More specifically, the present invention provides methods for the preparation of indolylquinones which involve the reaction of a 2,5-dihalo-1,4-benzoquinone of the formula II with at least one indole of the formula III. When one indole is used, a symmetrical bis-indolylquinone of the formula I is obtained as the product. In the alternative, step-wise or concurrent addition of two different indoles may be used to obtain an asymmetrical bis-indolylquinone of the formula VI. For example, an asymmetrical bis-indolylquinone may be made by the reaction of a 2,5-dihalo-1,4-benzoquinone with about one equivalent of a first indole, followed by addition of about 1.5 equivalents of a second indole. Preferably, the preparation of asymmetrical bis-indolylquinones is carried out in the presence of about 3 equivalents of metal carbonate. As another alternative, mixtures of two or more indoles may be reacted with the starting quinone to give a mixture of symmetrical and asymmetrical bis-indolylquinones. Finally, the controlled addition of one equivalent of at least one indole to the starting quinone in the presence of about one equivalent of metal carbonate can be used to obtain one or more mono-indolylquinones.

The preferred 2,5-dihalo-1,4-quinones useful in the present invention are the 2,5-dibromo-1,4-benzoquinones of formula II, which may be substituted or unsubstituted, wherein R1 and R2 are each independently Br, Cl, F, I, OH, H or —OCOR, wherein R is lower alkyl, aryl or alkylaryl. Alternatively, the 2,5-dichloro-, difluoro- or diiodo-1,4-benzoquinones may be used in the methods of the invention. A particularly preferred 2,5-dibromo-1,4-quinone is 2,3,5,6-tetrabromo-1,4-benzoquinone.

The indoles useful in the present invention may be substituted at the 1, 2, 3, 4, 5 or 7 positions with hydrogen, branched or unbranched $C_1$–$C_n$ alkyl, alkylcarboxy, $C_2$–$C_m$ alkenyl, $C_2$–$C_m$ alkynyl, alkenylcarboxy, aryl, akylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7. Preferably, the indoles used in the present invention are substituted at the 2 position. Least preferred indoles are the unsubstituted indoles. Certain indoles useful in the present invention are available from commercial sources such as the Aldrich Chemical Company, Milwaukee, Wis. Alternatively, the indoles may be prepared via a cyclization procedure according to the method of Verley and Bedure, 1925, *Bull. Soc. Chim. Fr.* (37): 190.

Any non-nucleophilic, aprotic solvent may be used in the 35 methods of the invention. Mixtures of solvents may also be used. Preferred solvents are inert or non-reactive, polar organic solvents including but not limited to acetonitrile, dimethyl formamide (DMF) and tetrahydrofuran (THF). A particularly preferred solvent is acetonitrile. The solvent volume will depend upon the scale of the reactors, and may range from a few milliliters up to a multi-liter volumes useful in large-scale production. Reactant concentrations are set forth below.

It is believed that the metal carbonate used in the methods of the present invention assists the reaction of the 2,5-dihalo-1,4-quinone and the indole by scavenging the hydrogen bromide by-product formed in the reaction. Any metal carbonate or mixture of metal carbonates may be used; however, cesium carbonate, potassium carbonate, sodium carbonate, lithium carbonate and mixtures thereof are preferred. A particularly preferred metal carbonate is cesium carbonate. The amount of metal carbonate used in the method ranges from about 2 to about 10 equivalents based on the haloquinone; preferably 2 to 5 equivalents; and most preferably 3 to 4 equivalents.

The reaction may be run at any concentration ranging from about 0.1M to about 5M (molarity based on the haloquinone). Preferably the reaction is run at a concentration of about 1M.

As mentioned above, the reaction to produce a mono-indolylquinone is preferably carried out in the presence of about two equivalents of metal carbonate. Reactions to produce symmetrical or asymmetrical bis-indolylquinones are preferably carried out in the presence of about 3 equivalents of metal carbonate.

According to the methods of the invention, the reaction of the 2,5-dihalo-1,4-quinone with the indole may be run at temperatures ranging from about −10° C. to about 100° C. However, a particularly beneficial aspect of the present invention is that harsh conditions and high temperatures are not required to effect this reaction. Preferably the reaction of the 2,5-dihalo-1,4-quinone is run at a temperature in the range of about 0° C. to about 30° C. More preferably, the reaction is run at about room temperature.

The reaction of the 2,5-dihalo-1,4-quinone with the indole may be conducted under an inert atmosphere such as nitrogen or argon; however, the reaction may also be run in atmospheric air. The reaction may be run at any pressure up to 500 psig; however, it is preferable to conduct the reaction at atmospheric pressure.

The reaction time will vary according to the specific, reactants and reaction conditions used, but generally will be from about 2 hours to about 72 hours.

After reaction of the 2,5-dihalo-1,4-quinone and the indole, the product indolylquinones are typically isolated according to standard workup procedures. For example, the crude reaction mixture may be diluted with 1N hydrochloric acid, followed by extraction with an organic solvent such as ethyl acetate. Typically, the organic layer is washed with brine and then dried over anhydrous sodium sulfate. As an alternative to extraction, the crude reaction mixture may simply be filtered to remove solids. The solvent is removed under reduced pressure, and the crude residue is purified by recrystallization, flash chromatography, High Pressure Liquid Chromatography (HPLC) or a combination thereof. Preferably, the residue is purified using flash chromatography and/or High Pressure Liquid chromatography (HPLC).

In a preferred embodiment, the symmetrical bis-indolylquinone of formula I is further reacted with an alkali metal hydroxide to give a bis-indol-2,5-dihydroxy-1,4-quinone of formula IV. Preferred alkali metal hydroxides are sodium and potassium hydroxide, or mixtures thereof. Preferably, this reaction is carried out in a mixture of ethanol and tetrahydrofuran using concentrated aqueous KOH at a reflux temperature of about 85° C. for up to 20 hours. The bis-indol-2,5-dihydroxy-1,4-quinone of formula IV maybe isolated according to standard workup and purification procedures as described above.

In other embodiments, the methods of the present invention comprise reacting a symmetrical compound of formula I wherein R1 and R2 are Br, or an asymmetrical compound of formula VI wherein R1 and R2 are Br, with an alkali metal hydroxide and an alcohol of the formula R'OH wherein R' is lower alkyl or alkylaryl, to a produce symmetrical indolylquinone of the formula V or an asymmetrical indolylquinone of formula XI.

As used herein the term "substituted or unsubstituted" means that the group in question can be substituted with one or more substituents as desired; for example, substituents other than hydrogen such as Br, Cl, F, I, $NH_2$, NR2, $NO_2$, CN, COR, OH, OR, $SO_2$, alkyl, aryl, alkylaryl and the like may be used. On the contrary, unsubstituted groups do not contain any substituents.

By the term "alkyl" as used herein is meant a straight or branched chain saturated hydrocarbon group having from 1 to 12 carbons such as methyl, ethyl, isopropyl, n-butyl, s-butyl, t-butyl, n-amyl, isoamyl, n-hexyl, n-octyl and n-decyl; "alkenyl" and "alkynyl" are used to mean straight or branched chain hydrocarbon groups having from 2 to 12 carbons and unsaturated by a double or triple bond respectively, such as vinyl, allyl, propargyl, 1-methylvinyl, but-1-enyl, but-2-enyl, but-2-ynyl, 1 methylbut-2-enyl, pent-1-enyl, pent-3-enyl, 3-methylbut-1-ynyl, 1,1-dimethylallyl, hex-2-enyl and 1-methyl-1-ethylallyl; "alkylaryl" means the aforementioned alkyl groups substituted by a phenyl group such as benzyl, phenethyl, phenopropyl, 1-benzylethyl, phenobutyl and 2-benzylpropyl; "aryl" as used herein includes a monocyclic or bicyclic rings, wherein at least one ring is aromatic including aromatic or heteroaromatic hydrocarbons; the term "hydroxy-alkyl" means the aforementioned alkyl groups substituted by a single hydroxyl group such as 2-hydroxyethyl, 2-hydroxypropyl, 3-hydroxypropyl, 4-hydroxybutyl, 1-hydroxybutyl and 6-hydroxyhexyl.

Specific compounds which can be made according to the methods of the present invention are described by formula (XII) below. R1–R12 of the formula can be as listed in Table I following the formula. Illustrative preparations of these compounds are found in the working examples.

TABLE I

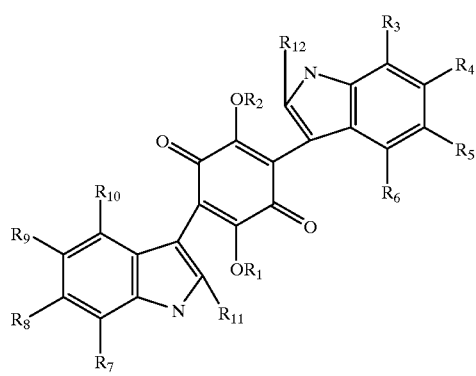

XII

| Ex. | Compound # | R1 = R2 | R11 | R12 | R3–R10[1] |
|---|---|---|---|---|---|
| 1. | (1) | H | 3-methyl-n-butyl | 3-methyl-n-butyl | |
| 2. | (1) | H | 3-methyl-n-butyl | 3-methyl-n-butyl | |
| 3. | (2) | H | n-butyl | n-butyl | |
| 4. | (3) | H | methyl | methyl | |
| 5. | (4) | H | 2-methylbut-2-en-4-yl | 2-methylbut-2-en-4-yl | |
| 6. | (5) | Ac | 2-methylbut-2-en-4-yl | 2-methylbut-2-en-4-yl | |
| 7. | (6) | Ac | 3-methyl-n-butyl | 3-methyl-n-butyl | |
| 8. | (1) | H | 3-methyl-n-butyl | 3-methyl-n-butyl | |
| 9. | (7) | H | H | H | R5 = R9 = Br |
| 10. | (8) | H | allyl | allyl | |
| 11. | (9) | H | n-propyl | n-propyl | |
| 12. | (10) | H | aminocarbonyl | aminocarbonyl | |
| 13. | (11) | Ac | aminocarbonyl | aminocarbonyl | |
| 14. | (12) | benzoyl | allyl | allyl | |
| 15. | (13) | H | cyano | cyano | |
| 16. | (14) | H | H | H | R6 = R10 = methoxycarbonyl |
| 17. | (15) | H | H | H | R3 = R5 = R7 = R9 = methoxy |
| 18. | (16) | H | H | H | R3 = R6 = R7 = R10 = methoxy |
| 19. | (17) | H | H | H | R5 = R9 = nitro |
| 20. | (18) | H | H | H | R6 = R10 = 4-chlorobenzoylamino |
| 21. | (19) | H | 4-chlorophenyl | 4-chlorophenyl | |
| 22. | (20) | H | 4-fluorophenyl | 4-fluorophenyl | |
| 23. | (21) | H | H | H | R4 = R6 = R8 = R10 = methoxy |
| 24. | (22) | H | H | H | R4 = R5 = R8 = R9 = methoxy |
| 25. | (23) | H | H | H | R6 = R10 = cyano |
| 26. | (24) | H | H | H | R5 = R9 = trifluoromethylphenyl-aminocarbonyl |
| 27. | (25) | H | 4-trifluoromethyl phenylaminocarbonyl | 4-trifluoromethyl phenylaminocarbonyl | |
| 28. | (26) | H | ethyl | ethyl | |
| 29. | (27) | H | H | H | R4 = R8 = NO2; R5 = R9 = Br |
| 30. | (28) | Me | 2-methylbut-2-en-4-yl | 2-methylbut-2-en-4-yl | |
| 31. | (29) | Me | 3-methyl-n-butyl | 3-methyl-n-butyl | |
| 32. | (1) | H | 3-methyl-n-butyl | 3-methyl-n-butyl | |
| 33. | (3) | H | methyl | methyl | |
| 34. | (26) | H | ethyl | ethyl | |
| 35. | (2) | H | n-butyl | n-butyl | |
| 36. | (31) | H | but-1-en-4-yl | but-1-en-4-yl | |
| 37. | (32) | H | 4-methyl-n-pentyl | 4-methyl-n-pentyl | |
| 38. | (33) | H | 2-phenylethyl | 2-phenylethyl | |
| 39. | (34) | H | H | 3-methyl-n-butyl | |
| 40. | (35) | H | ethyl | ethyl | R5 = R9 = carboxy |
| 41. | (36) | H | n-propyl | n-propyl | R5 = R9 = carboxy |
| 42. | (37) | H | 3-methyl-n-butyl | 3-methyl-n-butyl | R5 = R9 = carboxy |
| 43. | (38) | H | 4-carboxy-n-butyl | 4-carboxy-n-butyl | |
| 44. | (39) | H | H | 3-methyl-n-butyl | R5 = carboxy |
| 45. | (40) | H | ethyl | ethyl | R5 = R9 = amino |
| 46. | (41) | H | n-propyl | n-propyl | R5 = R9 = amino |
| 47. | (42) | H | 3-methyl-n-butyl | 3-methyl-n-butyl | R5 = R9 = amino |
| 48. | (6) | acetyl | 3-methyl-n-butyl | 3-methyl-n-butyl | |

TABLE I-continued

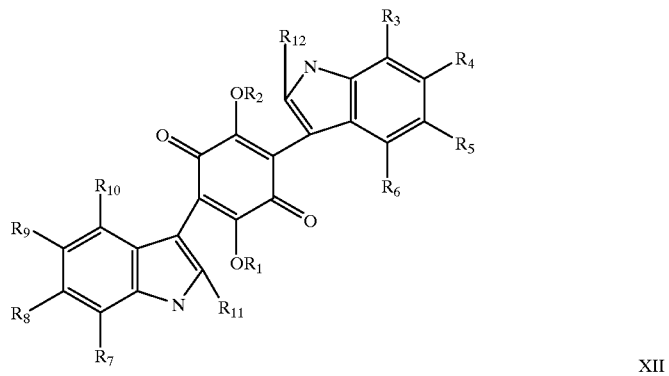

XII

| Ex. | Compound # | R1 = R2 | R11 | R12 | R3–R10[1] |
|---|---|---|---|---|---|
| 49. | (43) | H | ethyl | ethyl | R5 = R9 = 4-methylphenyl-sulfonylamino |
| 50. | (44) | H | n-propyl | n-propyl | R5 = R9 = 4-methylphenyl-sulfonylamino |
| 51. | (45) | H | 3-methyl-n-butyl | 3-methyl-n-butyl | R5 = R9 = 4-methylphenyl-sulfonylamino |
| 52. | (46) | H | 2-methylbut-1-en-4-yl | 2-methylbut-1-en-4-yl | |
| 53. | (47) | H | 2-methylpent-2-en-5-yl | 2-methylpent-2-en-5-yl | |
| 54. | (48) | H | phenyl | phenyl | |
| 55. | (49) | H | carboxy | carboxy | |
| 56. | (50) | H | methyl | carboxy | |
| 57. | (51) | H | methyl | phenyl | |
| 58. | (52) | H | 3-methyl-n-butyl | phenyl | |
| 59. | (53) | H | n-butyl | carboxy | |
| 60. | (54) | H | n-propyl | carboxy | |
| 61. | (55) | H | n-propyl | n-propyl | R4 = R8 = carboxy |

[1]Unless otherwise indicated, R3–R10 = hydrogen.

The mono-indolylquinone compounds which can be made according to the methods of the present invention are described by formula (XI) below. R1–R7 and R30 can be as listed in Table II below.

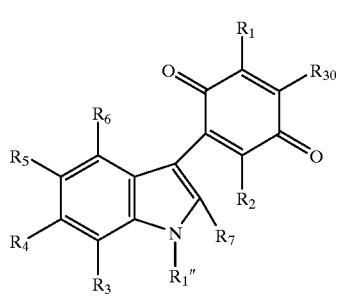

XI

The following is a general experimental procedure for the synthesis of the trihalo-monoindolyl quinones of formula XI using the appropriate indoles. As discussed above, the indoles may be commercially available or may be prepared according to the method of Verley and Bedure, 1925, Bull. Soc. Chim. Fr. (37): 190.

Preparation of 6-(2-phenylindol-3-yl)-2,3,5-tribromo-1,4-quinone [Compound (48a)]: To a 25 ml round bottom flask equipped with a magnetic stir bar and a drying tube was placed 2-phenylindole (2.28 g), cesium carbonate (7.69 g), bromanil (5 g), and acetonitrile (11.8 ml). After stirring the mixture at room temperature for 3 hours, 1N hydrochloric acid (150 ml) was added and the aqueous layer extracted with ethyl acetate (300 ml). The organic layer was washed with brine (150 ml) and dried with sodium sulfate. Following removal of the solvent under reduced pressure, the crude residue was purified by flash chromatography (10% ethyl acetate/hexane) to yield 6-(2-phenylindol-3-yl)-2,3,5-tribromo-1,4-quinone (1.88 g, 30%) as a blue crystalline solid.

TABLE II

| Compound # | R1 = R2 = R30 | R7 | R3-R6[2] |
|---|---|---|---|
| (1a) | Br | 3-methyl-n-butyl | |
| (2a) | Br | n-butyl | |

TABLE II-continued

| Compound # | R1 = R2 = R30 | R7 | R3-R6[2] |
|---|---|---|---|
| (3a) | Br | methyl | |
| (4a) | Br | 2-methylbut-2-en-4-yl | |
| (1a) | Br | 3-methyl-n-butyl | |
| (7a) | Br | H | R5 = Br |
| (8a) | Br | allyl | |
| (9a) | Br | n-propyl | |
| (10a) | Br | aminocarbonyl | |
| (13a) | Br | cyano | |
| (14) | Br | H | R6 = methoxycarbonyl |
| (15a) | Br | H | R3 = R6 = methoxy |
| (17a) | Br | H | R5 = nitro |
| (18a) | Br | H | R6 = 4-chlorobenzoylamino |
| (19a) | Br | 4-chlorophenyl | |
| (20a) | Br | 4-fluorophenyl | |
| (21a) | Br | H | R4 = R6 = methoxy |
| (22a) | Br | H | R4 = R5 = methoxy |
| (23a) | Br | H | R6 = cyano |
| (24a) | Br | H | R5 = trifluoro-methylphenylaminocarbonyl |
| (25a) | Br | 4-trifluoromethyl-phenylaminocarbonyl | |
| (26a) | Br | ethyl | |
| (27a) | Br | H | R4 = NO$_2$; R5 = Br |
| (1a) | Br | 3-methyl-n-butyl | |
| (31a) | Br | but-l-en-4-yl | |
| (32a) | Br | 4-methyl-n-pentyl | |
| (33a) | Br | 2-phenylethyl | |
| (34a) | Br | H | |
| (35a) | Br | ethyl | R5 = carboxy |
| (36a) | Br | n-propyl | R5 = carboxy |
| (37a) | Br | 3-methyl-n-butyl | R5 = carboxy |
| (38a) | Br | 4-carboxy-n-butyl | |
| (39a) | Br | H | R5 = carboxy |
| (40a) | Br | ethyl | R5 = amino |
| (41a) | Br | n-propyl | R5 = amino |
| (42a) | Br | 3-methyl-n-butyl | R5 = amino |
| (43a) | Br | ethyl | R5 = 4-methylphenyl-sulfonylamino |
| (44a) | Br | n-propyl | R5 = 4-methylphenyl-sulfonylamino |
| (45a) | Br | 3-methyl-n-butyl | R5 = 4-methylphenyl-sulfoylamino |
| (46a) | Br | 2-methylbut-1-en-4-yl | |
| (47a) | Br | 2-methylpent-2-en-5-yl | |
| (48a) | Br | phenyl | |
| (49a) | Br | carboxy | |
| (55a) | Br | n-propyl | R4 = R6 = carboxy |

[2]Unless otherwise indicated, R3-R6 = hydrogen.

As mentioned above, the compounds of Tables I and II have therapeutic activity for example as antifungal agents, antibacterial agents, and antitumor agents. In addition, these compounds may be useful in the dye industry.

5. WORKING EXAMPLES

In this section, examples of the methods described above are provided for illustration only and not by way of limitation. The reactants and starting materials are either readily synthesized or purchased from commercial sources.

Example 1
2,5-Dihydroxy-3,6-di-[2-(3-methyl-n-butyl)indol-3-yl]-1,4-quinone

1) Into a 250 ml round bottom flask, equipped with a magnetic stir bar, was placed 2-(3-methyl-n-butyl) indole (2.95 g), cesium carbonate (10.3 g) bromanil (3.34 g), and acetonitrile (79 ml). The mixture was stirred at room temperature for 45 hours. Following dilution with 1 N hydrochloric acid (250 ml), the crude mixture was extracted with ethyl acetate (500 ml). The organic layer was washed with brine (200 ml) and dried with sodium sulfate. After removal of solvent under reduced pressure, the crude residue was filtered through a short plug of flash silica, eluting with 20% ethyl acetate/hexane. The solvent was removed under reduced pressure, and the residue was purified by flash chromatography (15% ethyl acetate/hexane) to yield 2,5-dibromo-3,6-di-[2-(3-methyl-n-butyl)indol-3-yl]-1,4-quinone (553 g, 11%) as a blue crystalline solid.

Note: When the reaction was performed on 27.2 mg of starting indole, 95 mg cesium carbonate, 31 mg bromanil and 0.72 ml acetonitrile, the reaction was complete after 1.5 hours, and the product yield was 28%.

2) To a stirred solution of 2,5-dibromo-3,6-di-[2-(3-methyl-n-butyl)indol-3-yl]-1,4-quinone (553 mg), ethanol (9 ml), and tetrahydrofuran (9 ml) in a 100 ml round bottom flask equipped with a reflux condenser was added 2N aqueous potassium hydroxide solution (9 ml). The mixture was heated at 85° C. for 13 hours, followed by dilution with 1N aqueous sodium hydroxide solution (150 ml). The mixture was washed with 3:1 hexane/ethyl acetate (400 ml). After setting aside the aqueous layer, the organic layer was washed with another portion of 1N aqueous sodium hydroxide solution (150 ml) and then discarded. The basic aqueous layers were combined, acidified by adding 6N hydrochloric acid (60 ml), and extracted with ethyl acetate (300 ml). The organic layer was washed with brine (100 ml) and dried with sodium sulfate. Removal of solvent afforded 345 mg (78%) of 2,5-Dihydroxy-3,6-di-[2-(3-methyl-n-butyl)indol-3-yl]-1,4-quinone as a reddish-purple crystalline solid.

3) Preparation of 2-(3-methyl-n-butyl)-indole. Carbonyldiimidazole (65 g) was mixed with 500 ml of dry dichloromethane in a 2-L round bottom flask and stirred magnetically. A solution of 4-methylvaleric acid in 200 ml of dichloromethane was added dropwise over 45 minutes and the mixture was stirred for another 1.25 hours. o-Toluidine (45 g) in 100 ml of dichloromethane was then added over about 20 minutes. After stirring for 2 hours the mixture was washed with water and then the solvent was stripped on a rotary evaporator. The residue was mixed with 150 ml of methanol and 75 ml of water and put in the freezer. Filtration of the precipitate, dilution of the filtrate with water and refiltration of the precipitate gave 75 g (94%) of vacuum dried N-(2-methylphenyl)-4-methylvaleramide which was used without further treatment in the next step.

The following procedure is cited in *Bull. Soc. Chim. Fr.* (37):190 (1925). N-(2-methylphenyl)-4-methylvaleramide (20.5 g), sodium amide (90%) (11.0 g), and tetralin (100 ml) were mixed in a 500 ml round bottom flask equipped with a magnetic stirrer and reflux condenser and heated at reflux for 2 hours. After cooling to room temperature, ethanol (10 ml) was added, followed by H$_2$O (150 ml). The layers were separated, the organic layer was filtered through a pad of anhydrous magnesium sulfate, and the solution was placed in a 200 ml round bottom flask equipped with a 10-inch vacuum jacketed Vigreux column. Tetralin was distilled at 35–45° C./0.5 mm Hg. The residue was transferred to a 50 ml round bottom flask equipped with a 4-inch Vigreux column, and distillation at 118–129° C./0.5 mm Hg provided 2-(3-methyl-n-butyl)-indole 13.1 g (70%) as a slightly yellow solid.

Example 2

2,5-Dihydroxy-3,6-di-[2-(3-methyl-n-butyl)indol-3-yl]-1,4-quinone (larger scale)

1) Into a 250 ml round bottom flask, equipped with a magnetic stir bar, was placed 2-(3-methyl-n-butyl)indole (30.0 g), cesium carbonate (62.6 g) bromanil (27.2 g), and acetonitrile (64 ml). The mixture was stirred at room temperature for 20 hours. Following dilution with 1N hydrochloric acid (500 ml), the crude mixture was extracted with ethyl acetate (1 L). The organic layer was washed with brine (400 ml) and dried with sodium sulfate. The solvent was removed under reduced pressure, the residue was purified by flash chromatography (30% ethyl acetate/hexane) to yield a 1:1 mixture of the desired product, 2,5-dibromo-3,6-di-[2-(3-methyl-n-butyl)indol-3-yl]-1,4-quinone and the undesired by-product, 2,6-dibromo-3,5-di-[2-(3-methyl-n-butyl)indol-3-yl]-1,4-quinone (42.3 g, 46% yield of desired product by HPLC) as a blue crystalline solid.

2) To a stirred solution of 1:1 mixture of 2,5-dibromo-3, 6-di-[2-(3-methyl-n-butyl)indol-3-yl]-1,4-quinone and 2,6-dibromo-3,5-di[2-(3-methyl-n-butyl)indol-3-yl]-1,4-quinone (42.3 g), ethanol (166 ml), and tetrahydrofuran (166 ml) in a 1 L 3-necked round bottom flask equipped with a reflux condenser was added 4N aqueous potassium hydroxide solution (166 ml). The mixture was heated at 85° C. for 10 hours, followed by dilution with 1N hydrochloric acid (500 ml). The mixture was extracted with ethyl acetate (1 L).

The organic layer was washed with brine (250 ml) and dried with sodium sulfate. Removal of solvent afforded 35.1 g of crude (about 50% pure) 2,5-Dihydroxy-3,6-di-[2–3-methyl-n-butyl)indol-3-yl]-1,4-quinone to be purified by-HPLC.

In a separate experiment, purification of about 20 g of the crude product (about 50% pure) by HPLC resulted in 5 g of 2,5-Dihydroxy-3,6-di-[2-(3-methyl-n-butyl)indol-3-yl]-1,4-quinone with a purity of 97%.

Example 3

2,5-Dihydroxy-3, 6-di-(2-n-butyl-indol-3-yl)-1, 4-quinone

This compound was synthesized in the same manner as Example 2 except the starting indole was 2-n-butyl-indole. Preparation of 2-n-butyl-indole o-Toluidine (55 g) was mixed with 100 ml dry pyridine and 200 ml dry tetrahydrofuran in a 1-L 3-necked round bottom flask fitted with a Trubore stirrer, thermometer and a dropping funnel, under nitrogen. Then, with cooling in a refrigerated bath, valeryl chloride (60.3 g) was added dropwise over 1 hour. The mixture was stirred for another hour at room temperature and then poured onto 500 g ice and water. The precipitate was washed repeatedly with water on a Buchner funnel. The precipitate (88.9 g, 93%) was cyclized according to Verley and Bedure, 1925, *Bull. Soc. Chim. Fr.* (37): 190 to afford 2-n-butyl indole (67.4 g, 84%) as a very slightly yellow oil.

Example 4

2,5-Dihydroxy-3,6-di-[2-methyl-indol-3-yl]-1,4-quinone

This compound was synthesized in the same manner as Example 2 except the reaction time was 24 hours.

Example 5

2,5-Dihydroxy-3,6-di-[2-(2-methylbut-2-en-4-yl)indol-3-yl]1,4-quinone

This compound may be synthesized as follows:

A mixture of 100 mg of 2,5-diacetoxy-3,6-dibromo-1,4-quinone, 180 mg of 3-[2-(2-methylbut-2-en-4-yl)indole, prepared by the Fisher indole synthesis, 10 ml of anhydrous dimethylforamide, and powdered potassium carbonate, is heated at 100° C. for 24 hours. The cooled mixture is partitioned between ethyl acetate and water. The ethyl acetate layer is then washed with brine, dried over sodium sulfate, filtered and concentrated. The crude product is then purified on a medium pressure liquid chromatography column in a solvent mixture of dichloromethane and methanol to provide 25 mg of 2,5-diacetoxy-3,6-di-[2-(2-methylbut-2-en-4-yl)indol-3-yl]1,4-quinone. 2,5-Diacetoxy-3,6-di-[2 (2-methylbut-2-en-4-5 yl)indol-3-yl]1,4-quinone is then hydrolysed with 1 N aqueous sodium hydroxide solution in methanol. Acidification of the above mixture produces the crude product after filtration. Further crystallization in ethanol and water produces the title compound.

Other suitably protected quinones such as 3,6-dibromo-2,5-ditrimethylsiloxy-1,4-quinone, 3,6-dibromo-2,5-di-(t-butyldimethylsiloxy-1,4-quinone, 2,5-dibenzoxy-3,6-dibromo-1,4-quinone, 3,6-dibromo-2,5-diisobutyroxy-1,4-quinone, 2,5-dibenzyloxy-3,6-dibromo-1,4-quinone or 2,5-diallyoxycarbonyloxy-3,6-dibromo-1,4-quinone which can be prepared from commercially available 2,4-dibromo-3,6-dihydroxy-1,4-quinone may also be used as starting materials. These protecting groups can be removed by conventional deprotection methods such as diluted acid, potassium fluoride or palladium (0) complex or palladium on carbon with hydrogen or by methods described by Greene and Wuts (1991, "Protective Groups In Organic Synthesis," John Wiley and Son). Other solvents such as pyridine or dimethylsulfoxide (DMSO) may be used in place of dimethyl formamide.

Example 6
2,5-Diacetoxy-3,6-di-[2-(2-methylbut-2-en-4-yl)indol-3-yl]1,4-quinone 2,5-Diacetoxy-3,6-di-[2-(2-methylbut-2-en-4-yl)indol-3-yl]1,4-quinone is prepared as in Example 5.

Example 7
2,5-Diacetoxy-3,6-di-[2(3-methyl-n-butyl)indol-3-yl]1,4-quinone

Hydrogenation of 2,5-diacetoxy-3,6-di-[2-(2-methylbut-2-en-4-yl)indol-3-yl]1,4-quinone in methanol with 5% palladium on carbon under 1 atmosphere of hydrogen produced the title compound.

Example 8
2,5-Dihydroxy-3,6-di-[2-(3-methyl-n-butyl)indol-3-yl]1,4-quinone

Base hydrolysis of 2,5-diacetoxy-3,6-di-[2-(3-methyl-n-butyl)indol-3-yl]1,4-quinone as described in Example 5 produced the title compound.

Under similar conditions as those described in Examples 5 to 8, the following compounds are prepared using either 2,5-dibromo-3,6-dihydroxy-1,4-quinone or 2,3,5,6-tetrabromoquinone as starting materials:

Example 9
3,6-Di-[5-(bromo)indol-3-yl]-2,5-dihydroxy-1,4-quinone

Example 10
3,6-Di-[2-(allyl)indol-3-yl]-2,5-dihydroxy-1,4-quinone

Example 11
2,5-Dihydroxy-3,6-di-[2-(n-propyl)indol-3-yl]1,4-quinone

This compound was prepared under conditions similar to those described in Examples 5 to 8.

Example 12
3,6-Di-[2-(aminocarbonyl)indol-3-yl]-2,5-dihydroxy-1,4-quinone

Example 13
2,5-Diacetoxy-3,6-di-[2 (aminocarbonyl)indol-3-yl]-1,4-quinone

Example 14
3,6-Di-[2-allylindol-3-yl]-2,5-dibenzoyloxy-1,4-quinone

Example 15
2,5-Dihydroxy-3,6-di-[2-(cyano)indol-3-yl]1,4-quinone

Example 16
2,5-Dihydroxy-3,6-di-[4-(methoxycarbonyl)indol-3-yl]1,4-quinone

Example 17
2,5-Dihydroxy-3,6-di-[5,7-(dimethoxy)indol-3-yl]1,4-quinone

Example 18
2,5-Dihydroxy-3,6-di-[4,7-(dimethoxy)indol-3-yl]1,4-quinone

Example 19
2,5-Dihydroxy-3,6-di-[5-(nitro)indol-3-yl]1,4-quinone

Example 20
3,6-di-[4(4-chlorobenzoylamino)indol-3-yl]-2,5-dihydroxy-1,4-quinone

Example 21
3,6-di-[2-(4-chlorophenyl)indol-3-yl]-2,5-dihydroxy-1,4-quinone

Example 22
2,5-Dihydroxy-3,6-di-[2-(4-fluorophenyl)indol-3-yl]1,4-quinone

Example 23
2,5-Dihydroxy-3,6-di-[4,6-(dimethoxy)indol-3-yl]1,4-quinone

Example 24
2,5-Dihydroxy-3,6-di-[2-(5-hydroxy-6-methoxy)indol-3-yl]1,4-quinone

Example 25
2,5-Dihydroxy-3,6-di-[4-(cyano)indol-3-yl]1,4-quinone

Example 26
2,5-Dihydroxy-3,6-di-[5-(4-trifluoromethylphenylaminocarbonyl)indol-3-yl]1,4-quinone

Example 27
2,5-Dihydroxy-3,6-di-[2-(4-trifluoromethylphenylaminocarbonyl)indol-3-yl]1,4-quinone

Example 28
2,5-Dihydroxy-3,6-di-[2-(ethyl)indol-3-yl]1,4-quinone

This compound was prepared under conditions similar to those described in Examples 5 to 8.

Example 29
3,6-di-[2-(5-bromo-6-nitro)indol-3-yl]-2,5-dihydroxy-1,4-quinone

Example 30
2,5-Dimethoxy-3,6-di-[2-(2-methylbut-2-en-4-yl)indol-3-yl]1,4-quinone Methylation of Example 5 with methyl iodide and potassium carbonate in dimethylforamide followed by purification produces the title compound. This compound may also be prepared by heating 2,5-dibromo-3,6-di[2-(2-methylbut-2-en-4-yl)indol-3-y]1,4-quinone in methanol in the presence of powdered potassium carbonate.

Example 31
2,5-Dimethoxy-3,6-di-[2 (3-methyl-n-butyl)indol-3-yl]1,4-quinone

Hydrogenation of Example 30 under conditions as those in Example 3 produced the title compound.

Example 32
Preparation of 2,5-Dihydroxy-3,6-di-[2-(3-methyl-n-butyl)indol-3-yl]-1,4-quinone To a glass tube containing 2-(3-methyl-n-butyl)indole (400 mg), bromanil (431 mg) and potassium carbonate (703 mg) equipped with a magnetic stir bar, was added dimethylformamide (10 ml). The mixture was stirred at room temperature for 40 hours. Following dilution with 1N hydrochloric acid (100 ml), the crude mixture was extracted with ethyl acetate (200 ml). The organic layer was washed with brine (100 ml) and dried with sodium sulfate. After removal of solvent under reduced pressure, the crude residue was filtered through a short plug of flash silica, eluting with 30% ethyl acetate/hexane. The solvent was removed under reduced pressure, and the residue was purified by flash chromatography (15% ethyl acetate/hexane) to yield 2,5-dibromo-3,6-di-[2-(3-methyl-n-butyl)indol-3-yl]-1,4-quinone (40 mg, 7%) as a blue crystalline solid.

To a stirred solution of 2,5-dibromo-3,6-di-[2-(3-methyl-n-butyl)indol-3-yl]-1,4-quinone (40 mg) in methanol (1.5 ml) was added 2N methanolic sodium hydroxide (0.251 ml). The solution was stirred at room temperature for 24 hours, followed by dilution with water (50 ml). The product was extracted with ethyl acetate (100 ml), washed with brine (50 ml) and dried with sodium sulfate. Removal of solvent under reduced pressure provided 2,5-methoxy-3,6-di-[2-(3-methyl-n-butyl)indol-3-yl]-1,4-quinone (30 mg, 90%) as a yellow crystalline solid.

To a stirred solution of 2,5-dimethoxy-3,6-di-[2-(3-methyl-n-butyl)indol-3-yl]-1,4-quinone (9 mg) in ethanol (2 ml) was added 1 N aqueous potassium hydroxide (1 ml). The mixture was heated at 85° C. for 3.5 hours, then diluted with 1 N hydrochloric acid (25 ml). The product was extracted with ethyl acetate (50 ml), washed with brine (25 ml) and dried with sodium sulfate. The solvent was removed under reduced pressure to afford 2,5-dihydroxy-3,6-di[2-(3-methyl-n-butyl)indol-3-yl]-1,4-quinone (8 mg) as a reddish-brown stalline solid.

32a) Preparation of 2-(2-methyl-1-buten-4-yl)indole

To a stirred solution of 2-methylindole (1 g) in diethyl-ether (76 ml) under nitrogen was added a 1.6 M solution of n-butyllithium in hexane (14.3 ml) slowly dropwise via syringe. Potassium tert-butoxide (1.711 g) was then added, producing a bright yellow mixture. After stirring at room temperature under nitrogen for 50 minutes, the mixture was cooled to −78° C., whereupon 3-bromo-2-methylpropene (1.54 ml) was added dropwise via syringe, giving a red-orange solution. The reaction mixture was stirred at −78° C. for 2 hours, then quenched with water (10 ml). After warming to room temperature, water (150 ml) and 1 N hydrochloric acid (1 ml) was added to neutralize the reaction mixture. The mixture was extracted with ethyl acetate (250 ml), and the organic layer was washed with brine (100 ml) and dried with sodium sulfate. The solvent was removed under reduced pressure, and the crude residue was purified by flash chromatography (4% ethyl acetate/hexane) to afford 2-(2-methyl-1-butene-4-yl)indole (664 mg. 47%) as a waxy yellow solid.

32b) This indole is preferably synthesized by the method of Example 1. However, this indole may also be prepared as follows:

Preparation of 2-(3-methyl-n-butyl)indole

Into a 3-necked round bottom flask under a blanket of nitrogen was placed 5% palladium catalyst on charcoal (771 mg). A solution of 2-(2-methyl-1-buten-4-yl) indole (671 mg) in ethanol (36 ml) was added to the flask, which was evacuated and charged with hydrogen twice. The mixture was stirred vigorously under hydrogen (1 atmosphere) for 2 hours, followed by filtration through a pad of Celite. The solvent was removed under reduced pressure and the crude residue was purified by flash chromatography (3% ethyl acetate/hexane) to give 2-(3-methyl-n-butyl)indole (400 mg, 59%) as a yellow crystalline solid.

Example 33

Preparation of 2,5-Dihydroxy-3,6-di-[2-(methyl)indol-3-yl]-1,4-quinone

This compound is preferably synthesized by the method of Example 2 using 2-methylindole as the starting indole. However, this compound may also be prepared by the method of Example 32 using 2-methylindole as the starting indole.

Example 34

Preparation of 3,6-Di-(2-ethylindol-3-yl)-2,5-dihydroxy-1,4-quinone

This compound is preferably synthesized by the method of Example 2 using 2-ethylindole as the starting indole. However, this compound may also be prepared by the method of Example 32 using 2-ethylindole as the starting indole.

Preparation of 2-ethylindole: Refer to 32a) using methyl iodide as the alkylating agent.

Example 35

Preparation of 3,6-Di-(2-butylindol-3-yl) 2,5-dihydroxy-1,4-quinone: This compound is preferably synthesized by the method of Example 2 using 2-butylindole as the starting indole. Preparation of 2-butylindole: Refer to Example 3. However, this compound may also be prepared by the method of Example 32 using 2-butylindole as the starting indole.

Preparation of 2-(but-1-en-4-yl)indole: Refer to 32a) using allyl bromide as the alkylating agent. Preparation of 2-butylindole: Refer to 32b) using 2-(but-1-en-4-yl)indole as the starting material.

Example 36

Preparation of 3,6-Di-[2-(but-1-en-4-yl)indol-3-yl]2,5-dihydroxy-1,4-quinone

This compound is preferably synthesized by the method of Example 2 but may also be prepared according to the method of Example 32 using 2-(but-1-en-4-yl)indole as the starting indole.

Example 37

Preparation of 2,5-Dihydroxy-3,6-di-[2-(4-methyl-n-pentyl)indol-3-yl]-1,4-quinone: This compound is preferably synthesized by the method of Example 2 but may also be prepared according to Example 32 using 2-(4-methyl-n-pentyl) indole as the starting indole. Preparation of 2-(2-methyl-2-penten-5-yl)indole: Refer to Example 1 using 5-methylhexanoic acid as the starting acid. This indole may also be prepared according to Example 32a) using 4-bromo-2-methyl-2-butene as the alkylating reagent. Preparation of 2-(4-methyl-n-pentyl)indole: Refer to 32b) using 2-(2-methyl-2-penten-5-yl)indole as the starting material.

Example 38

Preparation of 2,5-Dihydroxy-3,6-di-[2-(2-phenylethyl)indol-3-yl]-1,4-quinone: This compound is preferably synthesized by the method of Example 2 but may also be prepared according to Example 32 using 2-(2-phenylethyl) indole as the starting indole. Preparation of 2-(2-phenylethyl)indole: Refer to Example 3 using 3-phenylpropionyl chloride as the starting acid chloride. This indole may also be prepared according to Example 32a) using benzyl bromide as the alkylating agent.

Example 39

Preparation of 2,5-Dihydroxy-6-(indol-3-yl)-3-[2-(3-methyl-n-butyl)indol-3-yl]-1,4-quinone This synthesis is achieved by treating 2-(3-methyl-n-butyl) indole with 2 equivalents of bromanil in the presence of cesium carbonate in dimethylformamide, followed by workup and purification similar to Example 32. The resultant mono-indolyl adduct is optionally treated with 2 equivalents of indole under the same conditions as above to provide the bis-indolyl product.

Example 40
Preparation of 3,6-Di-(5-carboxy-2-ethylindol-3-yl)-2,5-dihydroxy-1,4-quinone: Refer to Example 32 using 5-carboxy-2-ethylindole as the starting indole. Preparation of 5-carboxy-2-ethylindole: Refer to Example 3 using methyl 4-amino-3-methylbenzoate and propionyl chloride as the starting compounds. The methyl ester is hydrolyzed upon workup of the cyclization to give 5-carboxy-2-ethylindole. This synthesis may also be accomplished beginning with 5-chloro-2-methylindole, which is alkylated with methyl indole. The product chloroindole is converted to its Grignard species and exposed to carbon dioxide to finish the synthesis.

Example 41
Preparation of 3,6-Di-[5-carboxy-2-(n-propyl)indol-3-yl]-2,5-dihydroxy-1,4-quinone:

Refer to Example 32 using 5-carboxy-2-propylindole as the starting indole. Preparation of 5-carboxy-2-propylindole: Refer to Example 1 using methyl 4-amino-3-methyl-benzoate instead of o-toluidine or refer to 40 using ethyl iodide as the alkylating agent.

Example 42
Preparation of 3,6-Di-[5-carboxy-2-(3-methyl-n-butyl)indol-3-yl]-2,5-dihydroxy-1,4-quinone Refer to Example 32 using 5-carboxy-2-(3-methyl-n-butyl) indole as the starting indole. Preparation of 5-carboxy-2-(2-methyl-1-buten-4-yl)indole:

Refer to 40 using 3-bromo-2-methylpropene as the alkylating agent. Preparation of 5-carboxy-2-(3-methyl-n-butyl)indole: Refer to Example 1 using methyl 4-amino-3-methyl-benzoate instead of o-toluidine, or refer to Example 32b) using 5-carboxy-2-(2-methyl-l-buten-4-yl)indole as the starting material.

Example 43
Preparation of 3,6-Di-[2-(4-carboxy-n-butyl)indol-3-yl]-2,5-dihydroxy-1,4-quinone:

Refer to Example 32 using 2-(4-carboxy-n-butyl)indole as the starting indole. Preparation of 2-(4-carboxy-3-buten-1-yl)indole:

Refer to 32(a) using 4-bromo-2-butenoic acid as the alkylating agent. Preparation of 2-(4-carboxy-n-butyl) indole: Refer to Example 3 using methyl adipyl chloride as the acid chloride. The methyl ester was hydrolyzed in the cyclization workup to provide the product carboxyindole. In the alternative, refer to Example 32b) using 2-(4-carboxy-3-buten-1-yl)indole as the starting material.

Example 44
Preparation of 3-[5-Carboxy-2-(3-methyl-n-butyl)indol-3-yl]-2,5-dihydroxy-6-(indol-3-yl)-1,4-quinone Refer to Example 39 using 5-carboxy-2-(3-methyl-n-butyl) indole in the first step.

Example 45
Preparation of 3,6-Di-(5-amino-2-ethylindol-3-yl)-2,5-dihydroxy-1,4-quinone Refer to Example 32 using 5-amino-2-ethylindole as the starting indole. Preparation of 5-amino-2-ethylindole: Refer to Example 3 using 2-methyl-4-nitroaniline and propionyl chloride to give 5-nitro-2-ethylindole, which is reduced to the desired amino compound using catalytic hydrogenation as in 32b.

In the alternative, this synthesis may be accomplished with a standard nitration of 2-ethylindole using sodium nitrate and sulfuric acid similar to that cited in *Chem. Lett.* (7): 1125–1128 (1991). The resultant 5-nitro-2-ethylindole is reduced to the desired amino compound using catalytic hydrogenation as in 32b).

Example 46
Preparation of 3,6-Di-[5-amino-2-(n-propyl)indol-3-yl]-2,5-dihydroxy-1,4-quinone Refer to Example 32 using 5-amino-2-(n-propyl)indole as the starting indole. Preparation of 5-amino-2-(n-propyl) indole: Refer to Example 45 using butyryl chloride. In the alternative, refer to the synthesis cited in *Chem. Lett.* (7): 1125–1128 (1991) cited in Example 45 using 2-n-propylindole.

Example 47
Preparation of 3,6-Di-[5-amino-2-(3-methyl-n-butyl)indol-3-yl]2,5-dihydroxy-1,4-quinone Refer to Example 32 using 5-amino-2-(3-methyl-n-butyl) indole as the starting indole. Preparation of 5-amino-2-(3-methyl-n-butyl)indole: Refer to Example 1 using 2-methyl-4-nitroaniline instead of o-toluidine. The resultant 5-nitro-2-(3-methyl-n-butyl)-indole is reduced to the desired amino compound as in 32b. The synthesis may also be accomplished according to Example 45 using 2-(3-methyl-n-butyl) indole.

Example 48
Preparation of 2,5-Diacetoxy-3,6-di-[2-(3-methyl-n-butyl) indol-3-yl]-1,4-quinone This synthesis was accomplished by treating 2,5-hydroxy-3,6-di-[2-(3-methyl-n-butyl)indol-3-yl]1,4-quinone with acetic anhydride in the presence of pyridine.

Example 49
Preparation of 3,6-Di-[2-ethyl-5-(4-methylphenylsulfonylamino)indol-3-yl]-2,5-dihydroxy-1,4-quinone Refer to Example 32 using 2-ethyl-5-(4-methylphenylsulfonylamino)indole as the starting indole. Preparation of 2-ethyl-5-(4-methylphenylsulfonylamino) indole: The above compound is synthesized by treating 5-amino-2-ethylindole with p-toluenesulfonyl chloride in the presence of triethylamine.

Example 50
Preparation of 2,5-Dihydroxy-3,6-di-[5-(4-methylphenylsulfonylamino)-2-(n-propyl)indol-3-yl]-1,4-quinone Refer to Example 32 using 5-(4-methylphenylsulfonylamino)-2-(n-propyl)indole as the starting indole. Preparation of 5-(4-methylphenylsulfonylamino)-2-(n-propyl)indole: Refer to 49 using 5-amino-2-propylindole.

Example 51
Preparation of 2,5-Dihydroxy-3,6-di-[2-(3-methyl-n-butyl)-5-(4-methylphenylsulfonylamino)indol-3-yl]-1,4-quinone Refer to Example 32 using 2-(3-methyl-n-butyl)-5-(4-methylphenylsulfonylamino)indole as the starting indole. Preparation of 2-(3-methyl-n-butyl)-5-(4-methylphenylsulfonylamino)indole: Refer to 49 using 5-amino-2-(3-methyl-n-butyl)indole.

Example 52
Preparation of 2,5-Dihydroxy-3,6-di-[2-(2-methylbut-1-en-4-yl)indol-3-yl]-1,4-quinone Refer to Example 32 using 2-(2-methylbut-1-en-4-yl) indole as the starting indole.

Example 53
2,5-dihydroxy-2,6-di-[2-(2-methylpent-2-en-5-yl)-indol-3-yl]-1,4-quinone

Example 54
2,5-dihydroxy-3,6-di-(2-phenylindol-3-y-1)-1,4-quinone: Refer to Example 2 using 2-phenylindole as the starting indole.

Example 55
2,5-dihydroxy-3,6-di-(2-carboxyindol-3-yl)-1,4-quinone

Example 56
Preparation of 3-(2-carboxyindol-3-yl)-2,5-dihydroxy-6-(2-methylindol-3-yl)-1,4-quinone:

1) Into a 10 ml screw-cap glass tube was placed bromanil (1 g), cesium carbonate (2.3 g), ethyl indole-2-carboxylate (446 mg), and acetonitrile (2.36 ml). After stirring the mixture at room temperature for 3 hours, during which the mono-indolylquinone 6-(2-ethylcarboxyindol-3-yl)-2,3,5-tribromo-1,4-quinone was formed, 2-methylindole (464 mg) was added. The mixture was stirred at room temperature for 24 hours, after which 1 N hydrochloric acid (100 ml) was added. The aqueous layer was extracted with ethyl acetate (200 ml). The organic layer was washed with brine (100 ml) and dried with sodium sulfate. Following removal of the solvent under reduced pressure, the crude residue was purified by flash chromatography (30% ethyl acetate/hexane) to provide 2,5-dibromo-3-(2-ethylcarboxyindol-3-yl)-6-(2-methylindol-3-yl)-1,4-quinone (0.37 g) as a blue crystalline solid. Alternatively, the mono-indolylquinone 6-(2-ethylcarboxyindol-3-yl)-2,3,5-tribromo-1,4-quinone may isolated separately and used in further reactions with other indoles.

2) To a stirred solution of 2,5-dibromo-3-(2-ethylcarboxyindol-3-yl)-6-(2-methylindol-3-yl)-1,4-quinone (0.37 g), ethanol (1.6 ml), and tetrahydrofuran (1.6 ml) was added 4 N aqueous potassium hydroxide solution (1.6 ml). The mixture was heated at 85° C. for 10 hours, followed by dilution with 1 N hydrochloric acid (75 ml). The mixture was extracted with ethyl acetate (150 ml). The organic layer was washed with brine (75 ml) and dried with sodium sulfate. Removal of solvent afforded 3-(2-carboxyindol-3-yl)-2,5-dihydroxy-6-(2-methylindol-3-yl)-1,4-quinone (0.258 g) as a reddish brown crystalline solid.

Example 57
Preparation of 2,5-dihydroxy-6-(2-methylindol-3-yl)-3-(2-phenylindol-3-yl)-1,4-quinone. This compound was prepared according to the procedure of Example 56. It doesn't matter what order the two indoles are added in—the same product is obtained.

Example 58
Preparation of 2,5-dihydroxy-6-[2-(3-methyl-n-butyl)indol-3-yl]-3-(2-phenylindol-3-yl)-1,4-quinone. This compound was prepared according to the procedure of Example 56. As in Example 57, the order of addition of the two indoles doesn't matter.

Example 59
Preparation of 6-[2-(n-butyl)-indol-3-yl]-3-(2-carboxyindol-3-yl)-2,5-dihydroxy-1,4-quinone. This compound was prepared according to the procedure of Example 56.

Example 60
Preparation of 3-(2-carboxyindol-3-yl)-2,5-dihydroxy-6-[2-(n-propyl)-indol-3-yl]-1,4-quinone. This compound was prepared according to the procedure of Example 56.

Example 61
Preparation of 3,6-di(6-carboxy-2-n-propylindol-3-yl)-2,5-dihydroxy-1,4-quinone: Refer to Example 2 using 6-carboxy-2-n-propylindole as the starting indole. Preparation of 6-carboxy-2-n-propylindole: Refer to Example 3 using methyl 3-amino-4-methylbenzoate and butyryl chloride as the starting compounds. The methyl ester was hydrolyzed upon workup of the cyclization to give 6-carboxy-2-n-propylindole.

6. FORMULATION AND USE OF INDOLYLCUINONES

The compounds disclosed herein have utility, inter alia, at therapeutically effective doses to treat or ameliorate cell proliferative disorders involving PTK/adaptor protein interactions. The compounds prepared according to the present invention may be tested by a variety of methods for determining the ability of the compounds to inhibit kinase activity or to disrupt PTK/adaptor protein complexes.

Any assay currently used for screening compounds that act on cells containing PTKs can be used. In general, such assays involve exposing cells that express the PTK to a test substance and either: (a) scoring phenotypic changes in the cell culture as compared to control cells that were not exposed to the test substance; or (b) biochemically analyzing cell lysates to assess the level and/or identity of tyrosine phosphorylated proteins.

A common technique involves incubating cells with ligand and radiolabeled phosphate, lysing the cells, separating cellular protein components of the lysate using an SDS-polyacrylamide gel (SDS-PAGE) technique, in either one or two dimensions, and detecting the presence of phosphorylated proteins by exposing X-ray film. In a similar technique, the phosphorylated proteins are detected by immunoblotting techniques, in which case the phosphate that is detected is not radiolabeled. Instead, the cellular components separated by SDS-PAGE are transferred to a nitrocellulose membrane, where the presence of phosphorylated tyrosines is detected using an antiphosphotyrosine antibody (anti-PY). The anti-PY can be detected by labeling it with a radioactive substance, or an enzyme, such as horseradish peroxidase. A further alternative involves detecting the anti-PY by reacting with a second antibody which recognizes the anti-PY, this second antibody being labeled with either a radioactive moiety or an enzyme as previously described. Examples of these and similar techniques are described in Hansen et al., 1993, Electrophoresis 14:112–126; Campbell et al. 1993, *J. Biol. Chem.* 268:7427–7434; Donato et al., 1992, *Cell Growth and Diff.* 3:258–268; and Katagiri et al., 1993, *J. Immunol.* 150:585–593.

ELISA-type assays in microtitre plates can also be used to test purified substrates. See for example Peraldi et al., 1992, *J. Biochem.* 285: 71–78; Schraag et al., 1993, *Analytical Biochemistry* 211:233–239; Cleavland, 1990, *Analytical Biochemistry* 190:249–253; Farley, 1992, *Analytidal Biochemistry* 203:151–157; and Lozaro, 1991, *Analytical Biochemistry* 192:257–261. Examples of assay methods are described in U.S. application Ser. No. 08/279,321, filed Jul. 22, 1994 and U.S. application Ser. No. 08/488,156 filed Jun. 7, 1995 which are hereby incorporated in their entireties by reference.

A variety of methods may be used to assay the ability of the compounds prepared according to the invention to disrupt PTK/adaptor protein complexes. For example, in vitro complex formation may be assayed by, first, immobilizing one component, or a functional portion thereof, of the complex of interest to a solid support. Second, the immobilized complex component may be exposed to a compound prepared according to the present invention, and to the second component, or a functional portion thereof, of the complex of interest. Third, it may be determined whether or not the second component is still capable of forming a complex with the immobilized component in the presence of the compound.

Additionally, in vivo complex formation may be assayed by utilizing co-immunoprecipitation techniques well known to those of skill in the art. Briefly, a cell line capable of forming a PTK/adaptor complex of interest may be exposed to one or more of the compounds prepared according to the present invention, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

The effect of a compound of the invention on the transformation capability of the PTK/adaptor protein of interest may be directly assayed. For example, one or more of the compounds prepared according to the invention may be administered to a cell such as a fibroblast or hematopoietic cell capable of forming a PTK/adaptor complex which, in the absence of a compound of the invention, would lead to the cell's transformation (Muller, A. J. et al., 1991, *Mol. Cell. Biol.* 11:1785–1792; McLaughlin, J. et al., 1987, *Proc. Natl. Acad. Sci. USA* 84:6558–6562). The transformation state of the cell may then be measured in vitro, by monitoring, for example, its ability to form colonies in soft agar (Lugo and Witte, 1989, *Mol. Cell. Biol.* 9:1263–1270; Gishizky, M. L. and Witte, O. N., 1992, *Science* 256:836–839). Alternatively, a cell's transformation state may be monitored in vivo by determining its ability to form tumors in immunodeficient nude or severe combined immunodeficiency (SCID) mice (Sawyers, C. L. et al., 1992, *Blood* 79:2089–2098). Further, the ability of the compounds prepared according to the present invention, to inhibit various tumor cell lines, such as for example, melanoma, prostate, lung and mammary tumor cell lines established as SC xenografts can be examined.

Thus, the present invention also provides a method of ameliorating symptoms of a cell proliferative disorder wherein the cell proliferative disorder involves a protein tyrosine kinase polypeptide/adaptor polypeptide complex, with an amount of a compound of either of the formulas I or XI, sufficient to disrupt protein tyrosine kinase polypeptide/adaptor polypeptide complexes of the cell so that symptoms of the cell proliferative disorder are ameliorated.

The present invention also provides a method of ameliorating a cell proliferative disorder using a compound described herein, particularly a compound of the formula I, IV, V, VI, VIII, IX, X, XI, XII or XIII, wherein the cell proliferative disorder occurs in a mammal and the compound contacts the cell within a mammal so that the symptoms of the cell proliferative disorder in the mammal are ameliorated. The compounds, i.e., indolylquinones, of the present invention may be used alone or in combination with other drugs or therapies to treat cancer.

Cell proliferative disorders which are treatable according to the methods of the invention include BCR-ABL-associated cancers, gliomas, glioblastomas, melanomas, ovarian cancers, breast cancers, and prostate cancers.

Further, the present invention provides a method of ameliorating symptoms of a cell proliferative disorder wherein the cell proliferative disorder involves a. protein tyrosine kinase polypeptide/adaptor polypeptide complex, which involves contacting a cell capable of forming the protein tyrosine kinase polypeptide/adaptor polypeptide complex with an amount of a pharmaceutical composition comprising a compound of any one of the formulas I, IV, V, VI, VIII, IX, X, XI, XII or XIII, sufficient to disrupt protein tyrosine kinase polypeptide/adaptor polypeptide complexes of the cell so that symptoms of the cell proliferative disorder are ameliorated.

Further, the compounds prepared according to the present invention may be formulated into compositions comprising other drugs or pharmaceutical agents. In one embodiment, the pharmaceutical compositions of compounds prepared according to the present invention also comprise additional cancer treatment agents. For example, the compounds prepared according to the present invention may be formulated into pharmaceutical compositions in a conventional manner using one or more physiologically acceptable carriers or excipients. The compounds and their physiologically acceptable salts and solvates may also be formulated for administration by inhalation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents and other pharmaceutical agents as appropriate.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Such formulations may also comprise other pharmaceutical agents as appropriate. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Compounds prepared according to the present method may also be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds that can be prepared according to the present methods and their methods of use can also be found in United States patent application Ser. Nos. 08/476,136, filed Jun. 7, 1995 and 08/658,337, filed Jun. 5, 1996, each of which is hereby incorporated by reference.

EXAMPLE—In Vivo Activity of Compound #1

The following example illustrates the use of the compounds of the invention in an in vivo model of tumor growth.

Materials and Methods

Female athymic mice (BALB/c, nu/nu) were obtained from Simonsen Laboratories (Gilroy, Calif.). All animals were maintained under clean-room conditions in Micro-isolator cages with Alpha-dri bedding. They received sterile rodent chow and water ad libitum. A cell line established from a human epidermoid carcinoma (A431, ATCC CRL 1555) was grown in DMEM with 10% FBS and 2 mM GLN. All cell culture media, glutamine, and fetal bovine serum were purchased from Gibco Life Technologies (Grand Island, N.Y.) unless otherwise specified. All cells were grown in a humid atmosphere of 90–95% air and 5–10% $CO_2$ at 37° C. All cell lines were routinely subcultured twice a week and were negative for mycoplasma as determined by teh Mycotect method (Gibco). Cells were harvested at or near confluency with 0.05% Trypsin-EDTA and pelleted at 450×g for 10 min. Pellets were resuspended in sterile PBS or media (without FBS) to a particular concentration and the cells were implanted into the hindflank of the nice (8-1 mice per group). Tumor growth was measured over 3 to 6 weeks using venier calipers. Tumor volumes were calculated as a product of length ×width ×height unless otherwise indicated. P values were calculated using the Students' t-test. Compound 1 (from Example 1 and Table I) in 100 µL excipient (VPD:D5W, 1:1 (VPD- 12% w/v polysorbate 80, 0.55% citric acid (anhydrous), 35% w/v polyenthlene glycol (MW= 300 daltons) and 26.3% v/v 190 proof ethanol diluted 1:22 in 5% dextrose in water (D5W) was delivered by IP injection at different concentrations. Control animals received VPD:D5W alone. Animals were dosed daily on days 1–5 (high dose), days 1–9 (mid-dose) or throughout the study (low dose).

Results

The results are shown below as a percent tumor reduction compared to controls. Administration of compound I inhibited tumor growth in a dose dependent manner. Tumor growth remained inhibited even after cessation of treatment with the compound.

| Dosage mg/kg/day | Day | % inhibition | p-value |
|---|---|---|---|
| 2.5 | 7 | 11 | ns |
|  | 18 | 0 | ns |
| 5 | 7 | 30 | <0.01 |
|  | 18 | 38 | <0.01 |
| 7.5 | 7 | 55 | <0.01 |
|  | 18 | 50 | <0.01 |

The present invention is not to be limited in scope by the specific examples or embodiments described herein. These examples are, thus, not to be construed as limiting the scope of the invention in any way. Indeed, various modifications of the invention in addition to those described herein will become apparent to those skilled in the art from the foregoing description. Such modifications are intended to fall within the scope of the amended claims.

What is claimed is:

1. A compound of the formula:

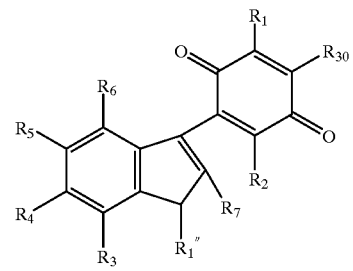

or a pharmaceutically acceptable salt thereof, wherein:

$R_1$ and $R_2$ are each individually Br, Cl, F, I, H, OH or —OCOR, wherein R is lower alkyl, aryl or alkylaryl;

$R_{30}$ is Br, Cl, F, I, OH or —OCOR, wherein R is lower alkyl, aryl or alkylaryl;

$R_1''$ is H, $C_1$–$C_7$ alkyl, $C_2$–$C_7$ alkenyl, $C_2$–$C_7$ alkynyl, arylalkyl or aryl;

$R_3$ to $R_7$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-metlhylbut-2-en-4-yl, wherein n is an integer from 0 to 12 and m is an integer of 2 to 12.

2. A compound of the formula:

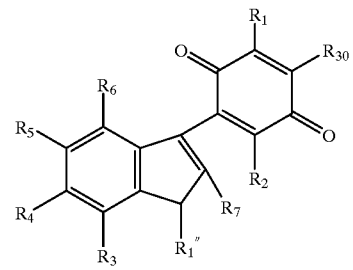

or a pharmaceutically acceptable salt thereof, wherein:

$R_2$ and $R_{30}$ are each individually Br, Cl, F, I, H, OH or —OCOR, wherein R is lower alkyl, aryl or alkylaryl;

$R_1$ is Br, Cl, F, I, OH or —OCOR, wherein R is lower alkyl, aryl or alkylaryl;

$R_1''$ is H, $C_1$–$C_7$ alkyl, $C_2$–$C_7$ alkenyl, $C_2$–$C_7$ alkynyl, arylalkyl or aryl; and $R_3$ to $R_7$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonlyl, sulfonamido, amino, mercapto, or 2-methylbut-2-en-4-yl, wherein n is an integer from 0 to 12 and m is an integer of 2 to 12.

3. A compound of the formula:

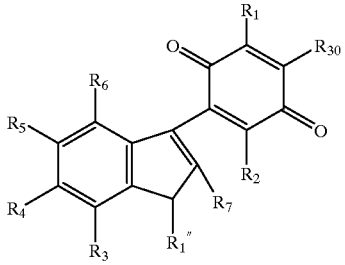

or a pharmaceutically acceptable salt thereof, wherein:

$R_1$ and $R_{30}$ are each individually Br, Cl, F, I, H, OH or —OCOR, wherein R is lower alkyl, aryl or alkylaryl;

$R_2$ is Br, Cl, F, I, OH or —OCOR, wherein R is lower alkyl, aryl or alkylaryl;

$R_1''$ is H, $C_1$–$C_7$ alkyl, $C_2$–$C_7$ alkenyl, $C_2$–$C_7$ alkynyl, arylalkyl or aryl; and $R_3$ to $R_7$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12 and m is an integer of 2 to 12.

4. A compound of the formula:

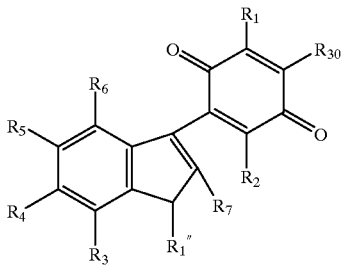

or a pharmaceutically acceptable salt thereof, wherein:

$R_1$, $R_2$ and $R_{30}$ are each individually Br, Cl, F, I, H, OH or —OCOR, wherein R is lower alkyl, aryl or alkylaryl;

$R_1''$ is $C_2$–$C_7$ alkynyl, arylalkyl or aryl;

$R_3$ to $R_7$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12 and m is an integer of 2 to 12.

5. A compound selected from the group consisting of compounds of the formula:

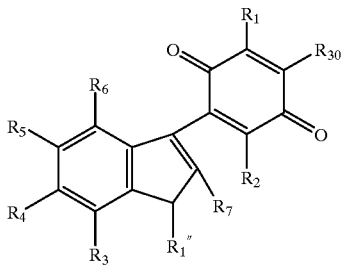

a) wherein $R_1$, $R_2$ and $R_{30}$ are Br, $R_7$ is 3-methyl-n-butyl, and $R_1''$ and $R_3$–$R_6$ are H;

b) wherein $R_1$, $R_2$ and $R_{30}$ are Br, $R_7$ is n-butyl, and $R_1''$ and $R_3$–$R_6$ are H;

c) wherein $R_1$, $R_2$ and $R_{30}$ are Br, $R_7$ is methyl, and $R_1''$ and $R_3$–$R_6$ are H;

d) wherein $R_1$, $R_2$ and $R_{30}$ are Br, $R_7$ is 2-methylbut-2-en-4yl, and $R_1''$ and $R_3$–$R_6$ are H;

e) wherein $R_1$, $R_2$ $R_5$ and $R_{30}$ are Br, and $R_1''$, $R_3$, $R_4$, $R_6$ and $R_7$ are H;

f) wherein $R_1$, $R_2$ and $R_{30}$ are Br, $R_7$ is allyl, and $R_1''$ and $R_3$–$R_6$ are H;

g) wherein $R_1$, $R_2$ and $R_{30}$ are Br, $R_7$ is n-propyl, and $R_1''$ and $R_3$–$R_6$ are H;

h) wherein $R_1$, $R_2$ and $R_{30}$, are Br, $R_7$ is aminocabonyl, and $R_1''$ and $R_3$–$R_6$ are II;

i) wherein $R_1$, $R_2$ and $R_{30}$ are Br, $R_7$ is cyano, and $R_1''$ and $R_3$–$R_6$ are H:

j) wherein $R_1$, $R_2$ and $R_{30}$ are Br, $R_6$ is methoxycarbonyl, and $R_1''$, $R_3$–$R_6$, and $R_7$ are H;

k) wherein $R_1$, $R_2$ and $R_{30}$ are Br, $R_3$ and $R_6$ are methoxy, and $R_1''$, $R_4$, $R_5$ and $R_7$ are H;

l) wherein $R_1$, $R_2$ and $R_{30}$ are Br, $R_5$ is nitro, and $R_1''$, $R_3$, $R_4$, $R_6$ and $R_7$ are H;

m) wherein $R_1$, $R_2$ and $R_{30}$ are Br, $R_6$ is 4-chlorobenzoylamino, and $R_1''$, $R_3$ $R_5$ and $R_7$ are H;

n) wherein $R_1$, $R_2$ and $R_{30}$ are Br, $R_7$ is 4-chlorophenyl, and $R_1''$ and $R_3$–$R_6$ are H;

o) wherein $R_1$, $R_2$ and $R_{30}$ are Br, $R_7$ is 4-fluorophenyl, and $R_1''$ and $R_3$–$R_6$ are H;

p) wherein $R_1$, $R_2$ and $R_{30}$ are Br, $R_1$ and $R_6$ are methoxy, and $R_1''$, $R_3$, $R_5$ and $R_7$ are H;

q) wherein $R_1$, $R_2$ and $R_{30}$ are Br, $R_4$ and $R_5$ are methoxy, and $R_1''$, $R_3$, $R_6$ and $R_7$ are H;

r) wherein $R_1$, $R_2$ and $R_{30}$ are Br, $R_6$ is cyano, and $R_1''$, $R_3$–$R_5$ and $R_7$ are H;

s) wherein $R_1$, $R_2$ and $R_{30}$ are Br, $R_5$ is trifluoromethylphenylaminocarbonyl and $R_1''$, $R_3$, $R_4$, $R_6$ and $R_7$ are H;

t) wherein $R_1$, $R_2$ and $R_{30}$ are Br, $R_7$ is 4-trifluoromethylphenylaminocarbonyl, and $R_1''$ and $R_3$ $R_6$ are H;

u) wherein $R_1$, $R_2$ and $R_{30}$ are Br, $R_7$ is ethyl, and $R_1''$ and $R_3$–$R_6$ are H;

v) wherein $R_1$, $R_2$ $R_5$ and $R_{30}$ are Br, $R_4$ is $NO_2$, and $R_1''$, $R_3$, $R_6$ and $R_7$ are H;

w) wherein $R_1$, $R_2$ and $R_{30}$ are Br, $R_7$ is but-1-en-4-yl, and $R_1''$ and $R_3$–$R_6$ are H;

x) wherein $R_1$, $R_2$ and $R_{30}$ are Br, $R_7$ is 4-methyl-n-pentyl, and $R_1''$ and $R_3$–$R_6$ are H;

y) wherein $R_1$, $R_2$ and $R_{30}$ are Br, $R_7$ is 2-phenylethyl, and $R_1''$ and $R_3$–$R_6$ are H;

z) wherein $R_1$, $R_2$ and $R_{30}$ are Br, and $R_1''$ and $R_3$–$R_7$ are H;

aa) wherein $R_1$, $R_2$ and $R_{30}$ are Br, $R_7$ is carboxy, $R_7$ is ethyl, and $R_1''$, $R_3$, $R_4$ and $R_6$ are H;

ab) wherein $R_1$, $R_2$ and $R_{30}$ are Br, $R_5$ is carboxy, $R_7$ is n-propyl, and $R_1''$, $R_3$, $R_4$ and $R_6$ are H;

ac) wherein $R_1$, $R_2$ and $R_{30}$ are Br, $R_5$ is carboxy, $R_7$ is 3-methyl-n-butyl, and $R_1''$, $R_3$, $R_4$ and $R_6$ are H;

ad) wherein $R_1$, $R_2$ and $R_{30}$ are Br, $R_7$ is 4-carboxy-n-butyl, and $R_1''$ and $R_3$–$R_6$ are H;

ae) wherein $R_1$, $R_2$ and $R_{30}$ are Br, $R_5$ is carboxy, and $R_1''$, $R_3$, $R_4$, $R_6$ and $R_7$ are H;

af) wherein $R_1$, $R_2$ and $R_{30}$ are Br, $R_5$ is amino, $R_7$ is ethyl, and $R_1''$, $R_3$, $R_4$ and $R_6$ are H;

ag) wherein $R_1$, $R_2$ and $R_{30}$ are Br, $R_5$ is amino, $R_7$ is n propyl, and $R_1''$, $R_3$, $R_4$ and $R_6$ are H;

ah) wherein $R_1$, $R_2$ and $R_{30}$ are Br, $R_5$ is amino, $R_7$ is 3-methyl-n-butyl, and $R_1''$, $R_3$, $R_4$ and $R_6$ are H;

ai) wherein $R_1$, $R_2$ and $R_{30}$ are Br, $R_5$ is 4-methylphenylsulfonylamino, $R_7$ is ethyl, and $R_1''$, $R_3$, $R_4$ and $R_6$ are H;

aj) wherein $R_1$, $R_2$ and $R_{30}$ are Br, $R_5$ is 4-methylphenylsulfonylamino, $R_7$ is n-propyl, and $R_1''$, $R_3$, $R_4$ and $R_6$ are II;

ak) wherein $R_1$, $R_2$ and $R_{30}$ are Br, $R_5$ is 4-methylphenylsulfonylamino, $R_7$ is 3-methyl-n-butyl, and $R_1''$, $R_3$, $R_4$ and $R_6$ are II;

al) wherein $R_1$, $R_2$ and $R_{30}$ are Br, $R_7$ is 2-methylbut-1-en-4-yl, and $R_1''$ and $R_3$–$R_6$ are H;

am) wherein $R_1$, $R_2$ and $R_{30}$ are Br, $R_7$ is 2-methylpent-2-en-5-yl, and $R_1''$ and $R_3$–$R_6$ are H;

an) wherein $R_1$, $R_2$ and $R_{30}$ are Br, $R_7$ is phenyl, and $R_1''$ and $R_3$–$R_6$ are H;

ao) wherein $R_1$, $R_2$ and $R_{30}$ are Br, $R_7$ is carboxy, and $R_1''$ and $R_3$–$R_6$ are H; and ap) wherein $R_1$, $R_2$ and $R_{30}$ are Br, $R_4$ and $R_6$ are carboxy, $R_7$ is n-propyl, and $R_1''$, $R_3$ and $R_6$ are H;

or a pharmacentically acceptable salt thereof.

6. A pharmaceutical composition which comprises a therapeutically effective amount of a compound of claim 1, 2, 3 or 4 and a pharmaceutically acceptable carrier or excipient.

* * * * *